US012565645B2

(12) United States Patent
Zhi et al.

(10) Patent No.: US 12,565,645 B2
(45) Date of Patent: Mar. 3, 2026

(54) METHODS OF SIZE EXCLUSION CHROMATOGRAPHY FOR THE CHARACTERIZATION OF RECOMBINANT ADENO-ASSOCIATED VIRUS COMPOSITIONS

(71) Applicant: REGENXBIO Inc., Rockville, MD (US)

(72) Inventors: Li Zhi, Bethesda, MD (US); Zhuchun Wu, North Potomac, MD (US)

(73) Assignee: REGENXBIO INC., Rockville, MD (US)

( * ) Notice: Subject to any disclaimer, the term of this patent is extended or adjusted under 35 U.S.C. 154(b) by 1183 days.

(21) Appl. No.: 17/602,199

(22) PCT Filed: Apr. 10, 2020

(86) PCT No.: PCT/US2020/027629
§ 371 (c)(1),
(2) Date: Oct. 7, 2021

(87) PCT Pub. No.: WO2020/210600
PCT Pub. Date: Oct. 15, 2020

(65) Prior Publication Data
US 2022/0275358 A1 Sep. 1, 2022

Related U.S. Application Data

(60) Provisional application No. 62/832,364, filed on Apr. 11, 2019, provisional application No. 62/839,182, filed on Apr. 26, 2019.

(51) Int. Cl.
| | |
|---|---|
| *C12N 15/10* | (2006.01) |
| *B01D 15/34* | (2006.01) |
| *C12N 7/00* | (2006.01) |
| *C12Q 1/6851* | (2018.01) |
| *C12Q 1/70* | (2006.01) |
| *G01N 1/44* | (2006.01) |
| *G01N 30/02* | (2006.01) |
| *G01N 30/74* | (2006.01) |

(52) U.S. Cl.
CPC .......... *C12N 15/101* (2013.01); *B01D 15/34* (2013.01); *C12N 7/00* (2013.01); *C12Q 1/701* (2013.01); *G01N 1/44* (2013.01); *G01N 30/74* (2013.01); *C12N 2750/14151* (2013.01); *C12Q 1/6851* (2013.01); *G01N 2030/027* (2013.01)

(58) Field of Classification Search
CPC .................. C12N 15/101; C12N 7/00; C12N 2750/14151; B01D 15/34; C12Q 1/701; C12Q 1/6851; G01N 1/44; G01N 30/74; G01N 2030/027
See application file for complete search history.

(56) References Cited

U.S. PATENT DOCUMENTS

| | | | |
|---|---|---|---|
| 6,783,972 B1 | 8/2004 | Byrne et al. | |
| 7,419,817 B2 * | 9/2008 | Chiorini .................. | C12N 7/00 |
| | | | 435/235.1 |
| 9,090,648 B2 | 7/2015 | Behr et al. | |
| 2007/0092866 A1 | 4/2007 | Bossis et al. | |
| 2008/0299545 A1 * | 12/2008 | Zhang ..................... | C12N 7/00 |
| | | | 435/5 |
| 2010/0105110 A1 | 4/2010 | Danthinne | |
| 2021/0041451 A1 * | 2/2021 | Jin ..................... | G01N 33/6848 |
| 2024/0254430 A1 * | 8/2024 | Zhang ............... | B01D 39/2068 |

FOREIGN PATENT DOCUMENTS

| | | |
|---|---|---|
| WO | 9708298 A1 | 3/1997 |
| WO | 99060146 A1 | 11/1999 |
| WO | 01025465 A1 | 4/2001 |
| WO | 2008/109721 A1 | 9/2008 |
| WO | 2012123430 A1 | 9/2012 |
| WO | 2014145578 A1 | 9/2014 |
| WO | 2018017956 A2 | 1/2018 |
| WO | 2018134419 A1 | 7/2018 |
| WO | 2019006390 A1 | 1/2019 |
| WO | 2019/212922 A1 | 11/2019 |

OTHER PUBLICATIONS

Tomono, T. et al. (2016). Ultracentrifugation-free chromatography-mediated large-scale purification of recombinant adeno-associated virus serotype 1 (rAAV1). Molecular Therapy. Methods & Clinical Development, 3(C), 15058-15058. (Year: 2016).*
Bartling, C. M., Andre, J. C., Howland, C. A., Hester, M. E., Cafmeyer, J. T., Kerr, A., Petrel, T., Petrikovics, I., & Rockwood, G. A. (2016). Stability Characterization of a Polysorbate 80-Dimethyl Trisulfide Formulation, a Cyanide Antidote Candidate. Drugs in R&D, 16(1), 109-127. (Year: 2016).*
Lloyd, L. L. (2014). Size-Exclusion Chromatography of Protein Aggregation in Biopharmaceutical Development and Production. LCGC Supplements, 32(4), 30-35. (Year: 2014).*
Tomono et al., Highly Efficient Ultracentrifugation-free Chromatographic Purification of Recombinant AAV Serotype 9, Molecular Therapy Methods & Clinical Development, 2018, vol. 11, pp. 180-190.
Li, Z. et al., "Analytical Technology Used in the Latest Development of Gene Therapy Candidates", Cell & Gene Therapy Insights, 2019; 5(4), 537-547. DOI: 10.18609/cgti.2019.059.
Sommer J M et al: "Quantification of Adeno-Associated Virus Particles and Empty Capsids by Optical Density Measurement", Molecular Therapy : The Journal of the American Society of Gene Therapy, Cell Press, US, vol. 7, No. 1, Jan. 1, 2003 (Jan. 1, 2003) pp. 122-128.

(Continued)

*Primary Examiner* — Janet L Andres
*Assistant Examiner* — Carey Alexander Stuart
(74) *Attorney, Agent, or Firm* — NIXON & VANDERHYE, PC

(57) ABSTRACT

The present disclosure relates to using size exclusion chromatography to isolate AAV genome, to determine the vector genome size purity of a composition comprising isolated rAAV particles, to assess the folding or secondary structure of vector genomes inside the capsids, and to determine vector genome titer (Vg) of a composition comprising isolated rAAV particles.

20 Claims, 8 Drawing Sheets

Specification includes a Sequence Listing.

(56)           References Cited

OTHER PUBLICATIONS

Maria Schnodt et al: "Improving the Quality of Adeno-Associated Viral Vector Preparations: The Challenge of Product-Related Impurities", Human Gene Therapy Methods, vol. 28, No. 3, Jun. 1, 2017 (Jun. 1, 2017), pp. 101-108.

Grieger Joshua C et al: "Production and characterization of adeno-associated viral vectors", Nature Protocols, Nature Publishing Group, GB, vol. 1, No. 3, Jan. 1, 2006 (Jan. 1, 2006) pp. 1412-1428.

Herb Runnels et al: "Gene Therapy and AAV: Advancing Analytical Characterization to Improve Product Understanding, Control and Comparability Exercises CMC Strategy Forum Jul. 17, 2017", Jun. 17, 2017 (Jun. 17, 2017), Retrieved from the Internet: URL: https : //cdn .ymaws . com/www. casss . org/resource/resmgr/ cmcnoamjulspkrslds/2017 CMCSRunnel sHerb.pdf, [retrieved on Jul. 13, 2020].

Weihong Qu et al: "Scalable Downstream Strategies for Purification of Recombinant Adeno-Associated Virus Vectors in Light of the Properties", Current Pharmaceutical Biotechnology, vol. 16, Jan. 1, 2015 (Jan. 1, 2015), pp. 684-695.

Eric Largy et al: "Shape matters: size-exclusion HPLC for the study of nucleic acid structural polymorphism", Nucleic Acids Research, vol. 42, No. 19, Aug. 20, 2014 (Aug. 20, 2014), pp. e149-e149.

Zhi Li et al: "Assessing Purity and Structures of AAV Vector Genomes by High Performance Size Exclusion Chromatography", Molecular Therapy : The Journal of the American Society of Gene Therapy; 22nd Annual Meeting of the Ameri can-Soci ety-of-Gene-and-Cell-Therapy (ASGCT); Washington, DC, USA; Apr. 29-May 2, 2019, Cell vol. 27, No. 4, Suppl. 1 Apr. 22, 2019 (Apr. 22, 2019), p. 92.

International Search Report and Written Opinion for PCT/US2020/ 027629 mailed Jul. 30, 2020.

Zhi et al., "Assessing Purity and Structure of AAV Vector Genomes by High Performance Size Exclusion Chromatography", Analytical Development, REGENXBIO, Inc., Rockville, MD, Apr. 9, 2019, 1 page.

Sepax Technologies, Inc., "Size Exclusion Chromatography—SRT— Better Surface Chemistry for Better Separation", Nov. 2013, 11 pages.

Tai et al., "Adeno-associated Virus Genome Population Sequencing Achieves Full Vector Genome Resolution and Reveals Human-Vector Chimeras", Molecular Therapy, Methods & Clinical Development, American Society of Gene & Cell Therapy, vol. 9, Jun. 2018, pp. 130-151.

Sepax Technologies, Inc., "SRT SEC Column Manual", Ver. 20180531, 2 pages.

* cited by examiner

METHODS OF SIZE EXCLUSION CHROMATOGRAPHY FOR THE CHARACTERIZATION OF RECOMBINANT ADENO-ASSOCIATED VIRUS COMPOSITIONS

CROSS-REFERENCE TO RELATED APPLICATIONS

This application is the U.S. National Phase of PCT Application No. PCT/US2020/027629, filed Apr. 10, 2020 which designated the U.S. and claims priority to U.S. Application Nos. 62/832,364 filed Apr. 11, 2019 and 62/839,182 filed Apr. 26, 2019, each of which is incorporated herein by reference in its entirety.

REFERENCE TO SEQUENCE LISTING SUBMITTED ELECTRONICALLY

The content of the electronically submitted sequence listing (Name 6728_0710_Sequence_Listing_ST25.txt; Size: 825 bytes; and Date of Creation: Sep. 12, 2025) is incorporated by reference in its entirety.

TECHNICAL FIELD

The present disclosure relates to using size exclusion chromatography to isolate AAV genome, and to characterize compositions comprising rAAV particles.

BACKGROUND

Recombinant adeno-associated virus (AAV)-based vectors are currently the most widely used gene therapy products in development. The preferred use of rAAV vector systems is due, in part, to the lack of disease associated with the wild-type virus, the ability of AAV to transduce non-dividing as well as dividing cells, and the resulting long-term robust transgene expression observed in clinical trials and that indicate great potential for delivery in gene therapy indications. Additionally, different naturally occurring and recombinant rAAV vector serotypes, specifically target different tissues, organs, and cells, and help evade any pre-existing immunity to the vector, thus expanding the therapeutic applications of AAV-based gene therapies. Before replication defective virus, for example, AAV based gene therapies can be more widely adopted for late clinical stage and commercial use, new methods for large scale production of recombinant virus particles need to be developed.

Product purity is a critical quality attribute for therapeutic biologics with the potential to impact safety and efficacy, thus assurance of control, including release testing, is critical. The AAV vector genome is delivered to the cell nucleus and can be persistent for a long period, much longer than that for capsid proteins. Thus, it is desirable to assess the vector genome purity for AAV products. The relative purity of intact AAV that quantify the empty and full capsid ratio can be determined by Analytical Ultracentrifugation (AUC), cryo-electron microscopy, and ion-exchange chromatography. In addition, the presence of vectors with fragmented genomes and non-transgene-related DNA contaminants, often referred to as partially-filled capsids, can be resolved by AUC. Capsid protein purity can be determined by SDS-PAGE or SDS-CGE. While a few studies have been published to analyze AAV genome by capillary and gel electrophoresis, no consensus method has been established for AAV genome purity.

Thus, there is a need in the art for methods to assess AAV vector genome purity and structure with high sensitivity and high reproducibility.

BRIEF SUMMARY

In one aspect, the disclosure provides a method of isolating recombinant adeno-associated virus (rAAV) genome using size exclusion chromatography. In some embodiments, the method comprises subjecting a composition comprising rAAV particles to a condition under which the rAAV particles are denatured prior to subjecting the composition comprising the denatured rAAV particles to size exclusion chromatography. In some embodiments, the mobile phase for the size exclusion chromatography comprises a salt, organic solvent, or detergent. In some embodiments, the mobile phase further comprises a buffering agent. In some embodiments, the rAAV comprises a capsid protein of the AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 serotype. In some embodiments, the rAAV comprises a capsid protein of the AAV-8 or AAV-9 serotype.

In a further aspect, the disclosure provides a method to characterize recombinant adeno-associated virus (rAAV) particles using size exclusion chromatography. Characterization of isolated rAAV particles includes but is not limited to determining vector genome size purity of a composition comprising isolated rAAV particles, assessing the folding or secondary structure of vector genomes inside the capsids, and determining vector genome titer (Vg) of a composition comprising isolated rAAV particles. In some embodiments, the mobile phase for the size exclusion chromatography comprises a salt, organic solvent, or detergent. In some embodiments, the mobile phase further comprises a buffering agent. In some embodiments, the rAAV comprises a capsid protein of the AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 serotype. In some embodiments, the rAAV comprises a capsid protein of the AAV-8 or AAV-9 serotype.

In some embodiments, a method disclosed herein is suitable for batch release, e.g. for batch release testing and/or lot release testing. In some embodiments, a method disclosed herein is performed as part of lot release testing.

In some embodiments, the disclosure provides:

[1.] A method of isolating recombinant adeno associated virus (rAAV) genome comprising
  a) subjecting a composition comprising rAAV particles to a condition under which the rAAV particles are denatured; and
  b) subjecting the composition comprising the denatured rAAV particles to size exclusion chromatography, wherein the mobile phase for the size exclusion chromatography comprises a salt, organic solvent, or detergent;

[2.] the method of [1] further comprising recovering the AAV genome;

[3.] the method of [1 further comprising measuring the eluate's UV absorbance at one or both of about 260 nm and at about 280 nm;

[4.] a method of determining the vector genome size purity of a composition comprising isolated rAAV particles, wherein the method comprises a) subjecting the composition to a condition under which the rAAV particles are denatured;

b) subjecting the composition comprising the denatured rAAV particles to size exclusion chromatography;

c) measuring the eluate's UV absorbance at one or both of about 260 nm and at about 280 nm; and d) determining the vector genome size purity of the composition comprising rAAV particles, wherein the mobile phase for the size exclusion chromatography comprises a salt, organic solvent, or detergent;

[5.] a method of assessing the folding or secondary structure of AAV vector genomes inside the capsids, wherein the method comprises a) subjecting the composition to a condition under which the rAAV particles are denatured;

b) subjecting the composition comprising the denatured rAAV particles to size exclusion chromatography; and c) measuring the eluate's UV absorbance at one or both of about 260 nm and at about 280 nm, wherein the mobile phase for the size exclusion chromatography comprises a salt, organic solvent, or detergent;

[6.] a method of determining vector genome titer (Vg) of a composition comprising isolated rAAV particles, wherein the method comprises a) subjecting the composition to a condition under which the rAAV particles are denatured;

b) subjecting the composition comprising the denatured rAAV particles to size exclusion chromatography;

c) measuring the eluate's UV absorbance at one or both of about 260 nm and at about 280 nm; and d) determining the Vg of the composition comprising rAAV particles, wherein the mobile phase for the size exclusion chromatography comprises a salt, organic solvent, or detergent;

[7.] the method of any one of [1] to [6], wherein subjecting the composition to a condition under which the rAAV particles are denatured comprises exposing the composition to a condition that substantially maximizes the dsDNA SEC signal;

[8.] the method of any one of [1] to [6], wherein subjecting the composition to a condition under which the rAAV particles are denatured comprises exposing the composition to a temperature that is no more than 10° C. above the minimum temperature needed to denature substantially all viral genome in the composition;

[9.] the method of any one of [1] to [6], wherein subjecting the composition to a condition under which the rAAV particles are denatured comprises subjecting the composition to a condition that results in a % Fragment DNA determination that correlates with the % Partial-filled capsid of the same composition determined by AUC;

[10.] the method of any one of [1] to [6], wherein subjecting the composition to a condition under which the rAAV particles are denatured comprises exposing the composition to thermal denaturation that substantially maximizes the dsDNA SEC signal;

[11.] the method of any one of [1] to [6], wherein subjecting the composition to a condition under which the rAAV particles are denatured comprises subjecting the composition to thermal denaturation that results in a % Fragment DNA determination that correlates with the % Partial-filled capsid of the same composition determined by AUC;

[12.] the method of any one of [1] to [6], wherein subjecting the composition to a condition under which the rAAV particles are denatured comprises incubating the composition at a temperature between about 65° C. and about 95° C., optionally between about 70° C. and about 90° C., between about 75° C. and about 85° C., or between about 80° C. and about 85° C.;

[13.] the method of [12], wherein the incubating is at about 70° C., about 75° C., about 80° C., about 85° C., or about 90° C.;

[14.] the method of [12], wherein the incubating is at about 75° C.;

[15.] the method of [12], wherein the incubating is at about 80° C.;

[16.] the method of [12], wherein the incubating is at about 85° C.;

[17.] the method of any one of to [16], wherein subjecting the composition to a condition under which the rAAV particles are denatured comprises incubating the composition at a temperature between about 65° C. and about 95° C. for between about 5 minutes and 60 minutes;

[18.] the method of [17], wherein the incubating is for about 10 minutes, about 15 minutes, about 20 minutes, about 25 minutes, about 30 minutes, about 35 minutes, about 40 minutes, about 45 minutes, or about 60 minutes;

[19.] the method of [17], wherein the incubating is for about 10 minutes;

[20.] the method of [17], wherein the incubating is for about 15 minutes;

[21.] the method of [17], wherein the incubating is for about 20 minutes;

[22.] the method of any one of to [21], wherein subjecting the composition to a condition under which the rAAV particles are denatured comprises incubating the composition at a temperature between about 65° C. and about 95° C. for between about 5 minutes and 60 minutes in the presence of a detergent;

[23.] the method of [22], wherein the detergent comprises SDS, trimethyl ammonium bromide (ETMAB), polysorbate 80, polysorbate 20, Pluronic F-68, or a combination thereof;

[24.] the method of [22], wherein the detergent has a concentration between about 0.005% and about 0.5%;

[25.] the method of [22], wherein the detergent comprises between about 0.005% and about 0.5% SDS;

[26.] the method of [22], wherein the detergent comprises about 0.05% SDS;

[27.] the method of any one of to [26], wherein substantially all viral particles in the sample are denatured by the denaturation process;

[28.] the method of any one of to [26], wherein at least about 95% of the viral particles in the sample are denatured by the denaturation process;

[29.] the method of any one of [1] to [28], wherein subjecting the composition comprising the denatured rAAV particles to size exclusion chromatography comprises contacting the composition with a size exclusion chromatography resin comprising a nominal pore size between about 50 nm and about 500 nm;

[30.] the method of [29], wherein the nominal pore size is about 100 nm, 200 nm, 300 nm, or 400 nm;

[31.] the method of [29], wherein the nominal pore size is about 200 nm;

[32.] the method of any one of [1] to [31], wherein size exclusion chromatography comprises the use of a High Performance Liquid Chromatography or Ultra-High Performance Liquid Chromatography system;

[33.] the method of any one of [1] to [32], wherein the mobile phase for the size exclusion chromatography comprises a salt, organic solvent, and detergent;

[34.] the method of any one of [1] to [33], wherein the mobile phase comprises a salt selected from the group consisting of sodium chloride, sodium acetate, sodium bicarbonate, sodium carbonate, ammonium carbonate, ammonium chloride, ammonium nitrate, and combinations thereof;

[35.] the method of [34], wherein the mobile phase comprises sodium chloride;

[36.] the method of any one of [1] to [35], wherein the mobile phase comprises a detergent selected from the group consisting of polysorbate 80, poloxamer 188, poloxamer 407, polysorbate 20, Pluronic F-68, or BRIJ 35, and combinations thereof;

[37.] the method of [36], wherein the mobile phase comprises polysorbate 80;

[38.] the method of any one of [1] to [37], wherein the mobile phase comprises an organic solvent selected from the group consisting of methanol, isopropanol, acetonitrile, dimethyl sulfoxide (DMSO), tetrahydrofuran (THF), trifluoroethanol (TFE), hexafluoroisopropanol (HFIP), and combinations thereof;

[39.] the method of [38], wherein the mobile phase comprises methanol;

[40.] the method of any one of [1] to [39], wherein the mobile phase for the size exclusion chromatography further comprises a buffering agent;

[41.] the method of [40], wherein the buffering agent is selected from the group consisting of sodium phosphate, histidine, sodium citrate, HEPES, MES, Tris, Bis-Tris, MOPS, TES, Bicine, glycine, Tricine, N-glycylglycine, sodium acetate, sodium carbonate, glycyl glycine, lysine, arginine, and combinations thereof;

[42.] the method of [40], wherein the buffering agent is sodium phosphate;

[43.] the method of any one of [1] to [42], wherein the mobile phase for the size exclusion chromatography comprises sodium phosphate, sodium chloride, polysorbate 80, and methanol;

[44.] the method of [43], wherein the mobile phase comprises between about 5 mM and about 50 mM sodium phosphate, between about 100 mM and about 500 mM sodium chloride, between about 0.01% and about 0.5% polysorbate 80, and between about 5% and about 50% methanol and has a pH between about 6.0 and 8.5;

[45.] the method of [43], wherein the mobile phase comprises about 10 mM sodium phosphate, about 300 mM sodium chloride, about 0.05% polysorbate 80, and about 20% methanol and has a pH of about 7.5;

[46.] the method of any one of [1] to [45], wherein the composition comprising rAAV particles comprises between about 2E+10 genome copy/ml and about 1E+14 genome copy/ml.

In some embodiments, a method disclosed herein comprises producing a stable formulation comprising recombinant adeno-associated virus (rAAV) particles, wherein the rAAV particles are produced by isolating rAAV particles from a feed comprising an impurity (for example, rAAV production culture), wherein the method for isolating rAAV particles comprises one or more processing steps. In some embodiments, the processing is at least one of harvest of a cell culture, clarification of the harvested cell culture (e.g., by centrifugation or depth filtration), tangential flow filtration, affinity chromatography, anion exchange chromatography, cation exchange chromatography, size exclusion chromatography, hydrophobic interaction chromatography, sterile filtration. In further embodiments, the processing includes at least 2, at least 3, at least 4, at least 5, or at least 6 of harvest of a cell culture, clarification of the harvested cell culture (e.g., by centrifugation or depth filtration), tangential flow filtration, affinity chromatography, anion exchange chromatography, cation exchange chromatography, size exclusion chromatography, hydrophobic interaction chromatography, and sterile filtration. In some embodiments, the processing does not include centrifugation of the harvested cell culture.

The disclosure provides a method for producing a stable formulation comprising isolated recombinant adeno-associated virus (rAAV) particles, comprising (a) isolating rAAV particles from a feed comprising an impurity by one or more of centrifugation, depth filtration, tangential flow filtration, ultrafiltration, affinity chromatography, size exclusion chromatography, ion exchange chromatography, and hydrophobic interaction chromatography, (b) characterizing the isolated rAAV particles using a method disclosed herein, and (c) formulating the isolated rAAV particles.

The disclosure provides a method for producing a pharmaceutical unit dosage of a stable formulation comprising isolated recombinant adeno-associated virus (rAAV) particles, comprising (a) isolating rAAV particles from a feed comprising an impurity by one or more of centrifugation, depth filtration, tangential flow filtration, ultrafiltration, affinity chromatography, size exclusion chromatography, ion exchange chromatography, and hydrophobic interaction chromatography, (b) characterizing the isolated rAAV particles using a method disclosed herein, and (c) formulating the isolated rAAV particles.

Still other features and advantages of the compositions and methods described herein will become more apparent from the following detailed description when read in conjunction with the accompanying drawings.

BRIEF DESCRIPTION OF THE DRAWINGS

FIG. 2A. SEC profile of rAAV samples exposed to 65° C. for 10 min or to 75° C. for 10 min in the presence of 0.05% SDS is shown. UV absorbance at 260 nm is shown. Arrow indicates particles that were not denatured by treatment at 65° C. for 10 min. FIG. 2B. SEC profile of fully denatured rAAV sample and marker DNA fragments. Main vector DNA peak corresponds to full-length vector genome.

DETAILED DESCRIPTION

Figure 1:
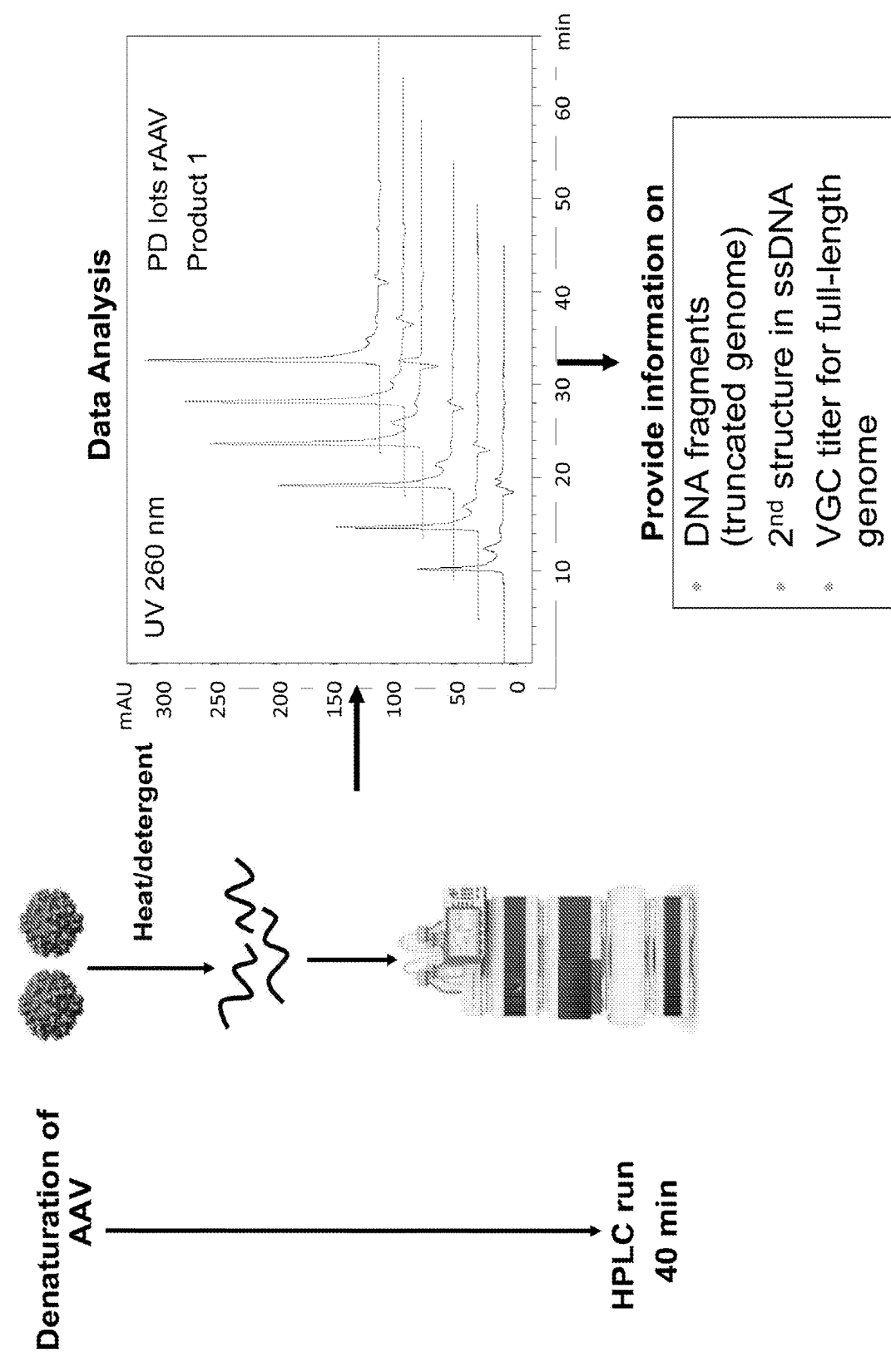
FIG. 1. Size exclusion HPLC for rAAV genome DNA analysis-method overview.

Provided herein is a method of isolating recombinant adeno-associated virus (rAAV) genome using size exclusion chromatography. In some embodiments, the method comprises subjecting a composition comprising rAAV particles to a condition under which the rAAV particles are denatured prior to subjecting the composition comprising the denatured rAAV particles to size exclusion chromatography. In some embodiments, the mobile phase for the size exclusion chromatography comprises a salt, organic solvent, or detergent. In some embodiments, the mobile phase further comprises a buffering agent.

Also provided is a method to characterize recombinant adeno-associated virus (rAAV) particles using size exclusion chromatography. Characterization of isolated rAAV particles includes but is not limited to determining vector genome size purity of a composition comprising isolated rAAV particles, assessing the folding or secondary structure of vector genomes inside the capsids, and determining vector genome titer (Vg) of a composition comprising isolated rAAV particles. In some embodiments, a method disclosed herein is used to support product development and process optimization by rapidly assessing the quality, e.g. purity, of rAAV particles produced by the modified processes. In some embodiments, a method disclosed herein is used to assess the quality of rAAV particles at different stages of an rAAV manufacturing process. In some embodiments, the rAAV comprises a capsid protein of the AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 serotype. In some embodiments, the rAAV comprises a capsid protein of the AAV-8 or AAV-9 serotype.

Definitions

Unless defined otherwise, all technical and scientific terms used herein have the same meaning as commonly understood by one of ordinary skill in the art to which this disclosure is related. To facilitate an understanding of the disclosed methods, a number of terms and phrases are defined below.

"About" modifying, for example, the quantity of an ingredient in the compositions, concentration of an ingredient in the compositions, flow rate, rAAV particle yield, feed volume, salt concentration, and like values, and ranges thereof, employed in the methods provided herein, refers to variation in the numerical quantity that can occur, for example, through typical measuring and handling procedures used for making concentrates or use solutions; through inadvertent error in these procedures; through differences in the manufacture, source, or purity of the ingredients employed to make the compositions or carry out the methods; and like considerations. The term "about" also encompasses amounts that differ due to aging of a composition with a particular initial concentration or mixture. The term "about" also encompasses amounts that differ due to mixing or processing a composition with a particular initial concentration or mixture. Whether or not modified by the term "about" the claims include equivalents to the quantities. In some embodiments, the term "about" refers to ranges of approximately 10-20% greater than or less than the indicated number or range. In further embodiments, "about" refers to plus or minus 10% of the indicated number or range. For example, "about 10%" indicates a range of 9% to 11%.

"AAV" is an abbreviation for adeno-associated virus, and may be used to refer to the virus itself or modifications, derivatives, or pseudotypes thereof. The term covers all subtypes and both naturally occurring and recombinant forms, except where required otherwise. The abbreviation "rAAV" refers to recombinant adeno-associated virus. The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), avian AAV, bovine AAV, canine AAV, equine AAV, primate AAV, non-primate AAV, and ovine AAV, and modifications, derivatives, or pseudotypes thereof. "Primate AAV" refers to AAV that infect primates, "non-primate AAV" refers to AAV that infect non-primate mammals, "bovine AAV" refers to AAV that infect bovine mammals, etc.

"Recombinant", as applied to an AAV particle means that the AAV particle is the product of one or more procedures that result in an AAV particle construct that is distinct from an AAV particle in nature.

A recombinant adeno-associated virus particle "rAAV particle" refers to a viral particle composed of at least one AAV capsid protein and an encapsidated polynucleotide rAAV vector genome comprising a heterologous polynucleotide (i.e. a polynucleotide other than a wild-type AAV genome such as a transgene to be delivered to a mammalian cell). The rAAV particle may be of any AAV serotype, including any modification, derivative or pseudotype (e.g., AAV-1, AAV-2, AAV-3, AAV-4, AAV-5, AAV-6, AAV-7, AAV-8, AAV-9, or AAV-10, or derivatives/modifications/pseudotypes thereof). Such AAV serotypes and derivatives/modifications/pseudotypes, and methods of producing such serotypes/derivatives/modifications/pseudotypes are known in the art (see, e.g., Asokan et al., Mol. Ther. 20 (4): 699-708 (2012).

The rAAV particles of the disclosure may be of any serotype, or any combination of serotypes, (e.g., a population of rAAV particles that comprises two or more serotypes, e.g., comprising two or more of rAAV2, rAAV8, and rAAV9 particles). In some embodiments, the rAAV particles are rAAV1, rAAV2, rAAV3, rAAV4, rAAV5, rAAV6, rAAV7, rAAV8, rAAV9, rAAV10, or other rAAV particles, or combinations of two or more thereof). In some embodiments, the rAAV particles are rAAV8 or rAAV9 particles.

In some embodiments, the rAAV particles have an AAV capsid protein of a serotype selected from the group consisting of AAV-1, AAV-2, AAV-3, AAV-4, AAV-5, AAV-6, AAV-7, AAV-8, AAV-9, AAV-10, AAV-11, AAV-12, AAV-13, AAV-14, AAV-15 and AAV-16 or a derivative, modification, or pseudotype thereof. In some embodiments, the rAAV particles have an AAV capsid protein of a serotype of AAV-8, AAV-9, or a derivative, modification, or pseudotype thereof.

The terms "purifying", "purification", "separate", "separating", "separation", "isolate", "isolating", or "isolation", as used herein, refer to increasing the degree of purity of a target product, e.g., rAAV particles and rAAV genome from a sample comprising the target product and one or more impurities. Typically, the degree of purity of the target product is increased by removing (completely or partially) at least one impurity from the sample. In some embodiments, the degree of purity of the rAAV in a sample is increased by removing (completely or partially) one or more impurities from the sample by using a method described herein.

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Where embodiments of the disclosure are described in terms of a Markush group or other grouping of alternatives, the disclosed method encompasses not only the entire group listed as a whole, but also each member of the group individually and all possible subgroups of the main group, and also the main group absent one or more of the group members. The disclosed methods also envisage the explicit exclusion of one or more of any of the group members in the disclosed methods.

Methods Using Size Exclusion Chromatography

In some embodiments, the disclosure provides methods of isolating recombinant adeno-associated virus (rAAV) genome using size exclusion chromatography. In some embodiments, a method disclosed herein comprises subjecting a composition comprising rAAV particles to a condition under which the rAAV particles are denatured prior to subjecting the composition comprising the denatured rAAV particles to size exclusion chromatography. In some embodiments, the mobile phase for the size exclusion chromatography comprises a salt, organic solvent, or detergent. In some embodiments, the mobile phase further comprises a buffering agent. In some embodiments, the mobile phase comprises sodium phosphate, sodium chloride, polysorbate 80, and methanol.

In some embodiments, the disclosure provides methods to characterize recombinant adeno-associated virus (rAAV) particles using size exclusion chromatography. Characterization of isolated rAAV particles includes but is not limited to determining vector genome size purity of a composition comprising isolated rAAV particles, assessing the folding or secondary structure of vector genomes inside the capsids, and determining vector genome titer (Vg) of a composition comprising isolated rAAV particles. In some embodiments, a method disclosed herein comprises subjecting a composition comprising rAAV particles to a condition under which the rAAV particles are denatured prior to subjecting the composition comprising the denatured rAAV particles to size exclusion chromatography. In some embodiments, the mobile phase for the size exclusion chromatography comprises a salt, organic solvent, or detergent. In some embodiments, the mobile phase further comprises a buffering agent.

In some embodiments, a method of isolating recombinant adeno-associated virus (rAAV) genome disclosed herein comprises (a) subjecting a composition comprising rAAV particles to a condition under which the rAAV particles are denatured; and (b) subjecting the composition comprising the denatured rAAV particles to size exclusion chromatography. In some embodiments, a method disclosed herein further comprises recovering the AAV genome. In some embodiments, a method disclosed herein further comprises determining AAV genome concentration in the eluate of the size exclusion chromatography. In some embodiments, AAV genome concentration in the eluate is determined by measuring UV absorbance at one or both of about 260 nm and at about 280 nm. In some embodiments, AAV genome concentration in the eluate is determined by measuring UV absorbance at about 260 nm.

In some embodiments, a method of determining the vector genome size purity of a composition comprising isolated rAAV particles comprises (a) subjecting a composition comprising rAAV particles to a condition under which the rAAV particles are denatured; (b) subjecting the composition comprising the denatured rAAV particles to size exclusion chromatography, and (c) determining AAV genome concentration in the eluate of the size exclusion chromatography. In some embodiments, AAV genome concentration in the eluate is determined by measuring UV absorbance at one or both of about 260 nm and at about 280 nm. In some embodiments, AAV genome concentration in the eluate is determined by measuring UV absorbance at about 260 nm. In some embodiments, a method disclosed herein further comprises determining the vector genome size purity of the composition comprising rAAV particles. In some embodiments, vector genome size purity is determined by analyzing relative peak areas of the UV absorbance curve.

In some embodiments, a method of assessing the folding or secondary structure of vector genomes inside the capsids comprises (a) subjecting a composition comprising rAAV particles to a condition under which the rAAV particles are denatured; (b) subjecting the composition comprising the denatured rAAV particles to size exclusion chromatography, and (c) determining AAV genome concentration in the eluate of the size exclusion chromatography.

In some embodiments, a method of determining vector genome titer (Vg) of a composition comprising isolated rAAV particles comprises (a) subjecting a composition comprising rAAV particles to a condition under which the rAAV particles are denatured; (b) subjecting the composition comprising the denatured rAAV particles to size exclusion chromatography, and (c) determining AAV genome concentration in the eluate of the size exclusion chromatography. In some embodiments, AAV genome concentration in the eluate is determined by measuring UV absorbance at one or both of about 260 nm and at about 280 nm. In some embodiments, AAV genome concentration in the eluate is determined by measuring UV absorbance at about 260 nm. In some embodiments, a method disclosed herein further comprises determining the vector genome titer (Vg) of the composition comprising rAAV particles.

In some embodiments, a method of characterizing a composition comprising isolated rAAV particles comprises (a) subjecting a composition comprising rAAV particles to a condition under which the rAAV particles are denatured; (b) subjecting the composition comprising the denatured rAAV particles to size exclusion chromatography, and (c) determining AAV genome concentration in the eluate of the size exclusion chromatography. In some embodiments, AAV genome concentration in the eluate is determined by measuring UV absorbance at one or both of about 260 nm and at about 280 nm. In some embodiments, AAV genome concentration in the eluate is determined by measuring UV absorbance at about 260 nm. In some embodiments, a method disclosed herein further comprises determining a characteristics of the composition comprising rAAV particles.

In some embodiments, a method disclosed herein comprises subjecting a composition comprising rAAV particles to a condition under which the rAAV particles are denatured. Any method known to one of skill in the art capable of denaturing rAAV capsid polypeptides can be used to practice a method disclosed herein. In some embodiments, the process for denaturing rAAV capsid polypeptides is also capable of denaturing the rAAV genome. In some embodiments, denaturing the rAAV particles comprises subjecting a composition comprising rAAV particles to a condition under which the rAAV genome is denatured. In some embodiments, denaturing the rAAV particles comprises subjecting a composition comprising rAAV particles to a condition under which both the rAAV capsid polypeptides and the rAAV genome are denatured. In some embodiments, denaturing the rAAV particles comprises exposing them to heat, for example, by incubating the composition comprising the rAAV particles at a temperature between about 65° C. and about 95° C. In some embodiments, the incubation temperature is between about 70° C. and about 90° C., between about 75° C. and about 85° C., or between about 80° C. and about 85° C. In some embodiments, the incubation temperature is between about 70° C. and about 90° C. In some embodiments, the incubation temperature is between about 75° C. and about 85° C. In some embodiments, the incubation temperature is between about 80° C. and about 85° C. In some embodiments, denaturing the rAAV particles comprises exposing them to a chaotropic agent. In some embodiments, denaturing the rAAV particles comprises exposing them to a detergent. In some embodiments, denaturing the rAAV particles comprises exposing them to at least two of heat, a chaotropic agent, and a detergent. In some embodiments, denaturing the rAAV particles comprises exposing them to heat in the presence of a detergent.

In some embodiments, denaturing the rAAV particles comprises exposing the particles to conditions that substantially maximizes the dsDNA SEC signal. In some embodiments, denaturing the rAAV particles comprises exposing the particles to conditions that substantially maximizes the dsDNA SEC signal of a reference composition comprising the same rAAV particles. Denaturation conditions that substantially maximize the dsDNA SEC signal for a rAAV composition can be determined using the methods disclosed herein, for example, by analyzing the DNA SEC profile of samples subjected to different denaturation conditions.

In some embodiments, the % Fragment DNA content of an rAAV composition determined using a method disclosed herein correlates with the % Partial-filled capsid of the same composition determined by AUC. In some embodiments, % Fragment DNA content determined using a method disclosed herein correlates with the % Partial-filled capsid determined by AUC when the difference between the two values is less than about 1, less than about 2, less than about 3, less than about 4, less than about 5, or less than about 10. In some embodiments, % Fragment DNA content determined using a method disclosed herein correlates with the % Partial-filled capsid determined by AUC when the difference between the two values is less than about 1. In some embodiments, % Fragment DNA content determined using a method disclosed herein correlates with the % Partial-filled capsid determined by AUC when the difference between the two values is less than about 3. In some embodiments, % Fragment DNA content determined using a method disclosed herein correlates with the % Partial-filled capsid determined by AUC when the difference between the two values is less than about 5. In some embodiments, denaturing the rAAV particles comprises subjecting a composition comprising the rAAV particles to conditions that results in a % Fragment DNA content determined using a method disclosed herein that correlates with the % Partial-filled capsid of the same composition determined by AUC.

In some embodiments of a method disclosed herein, denaturing the rAAV particles comprises exposing them to heat. As disclosed herein, the thermal denaturation conditions used to denature the AAV particles influences the subsequently obtained DNA-SEC profile. Suboptimal thermal denaturation, for example, by using temperature that does not denature substantially all viral genomes in the sample can lead to reduced dsDNA SEC signal and the presence of ssDNA SEC signal. Increasing the thermal denaturation temperature to achieve the denaturation of substantially all viral genomes in the sample can increase dsDNA SEC signal and reduce or eliminate ssDNA SEC signal. Excessive thermal denaturation, for example, by using temperature above the minimum needed to denature substantially all viral genomes in the sample, can lead to a loss of dsDNA SEC signal. Without being bound by any particular theory, excessive thermal denaturation may cause loss of material and/or create artificial DNA fragments. The dsDNA SEC signal loss due to excessive thermal denaturation can be related to vector sequence and DNA construct designs. Consequently, optimal thermal denaturation conditions can vary between different compositions comprising different rAAV particles. In some embodiments, denaturing the rAAV particles comprises exposing the particles to thermal denaturation under conditions that substantially maximizes the dsDNA SEC signal of a reference composition comprising the same rAAV particles. Thermal denaturation conditions that substantially maximizes the dsDNA SEC signal for a rAAV composition can be determined using the methods disclosed herein, for example, by analyzing the DNA SEC profile of samples subjected to different thermal denaturation conditions. In some embodiments, denaturing the rAAV particles comprises incubating the composition comprising rAAV particles at a temperature that is within 5° C. of the temperature that substantially maximizes the dsDNA SEC signal of a reference composition comprising the same rAAV particles. In some embodiments, denaturing the rAAV particles comprises incubating the composition comprising rAAV particles at a temperature that is within 10° C. of the temperature that substantially maximizes the dsDNA SEC signal of a reference composition comprising the same rAAV particles. In some embodiments, denaturing the rAAV particles comprises incubating the composition comprising rAAV particles at a temperature that is within 15° C. of the temperature that substantially maximizes the dsDNA SEC signal of a reference composition comprising the same rAAV particles.

In some embodiments, denaturing the rAAV particles comprises incubating the composition comprising rAAV particles at the minimum temperature needed to denature substantially all viral genomes in a reference composition comprising the same rAAV particles. In some embodiments, denaturing the rAAV particles comprises incubating the composition comprising rAAV particles at a temperature that is no more than 5° C. above the minimum temperature needed to denature substantially all viral genomes in a reference composition comprising the same rAAV particles. In some embodiments, denaturing the rAAV particles comprises incubating the composition comprising rAAV particles at a temperature that is no more than 10° C. above the minimum temperature needed to denature substantially all viral genomes in a reference composition comprising the same rAAV particles. In some embodiments, denaturing the rAAV particles comprises incubating the composition comprising rAAV particles at a temperature that is no more than 15° C. above the minimum temperature needed to denature substantially all viral genomes in a reference composition comprising the same rAAV particles.

In some embodiments, the % Fragment DNA content of an rAAV composition determined using a method disclosed herein correlates with the % Partial-filled capsid of the same composition determined by AUC. In some embodiments, % Fragment DNA content determined using a method disclosed herein correlates with the % Partial-filled capsid determined by AUC when the difference between the two values is less than about 1, less than about 2, less than about 3, less than about 4, less than about 5, or less than about 10. In some embodiments, % Fragment DNA content determined using a method disclosed herein correlates with the % Partial-filled capsid determined by AUC when the difference between the two values is less than about 1. In some embodiments, % Fragment DNA content determined using a method disclosed herein correlates with the % Partial-filled capsid determined by AUC when the difference between the two values is less than about 3. In some embodiments, % Fragment DNA content determined using a method disclosed herein correlates with the % Partial-filled capsid determined by AUC when the difference between the two values is less than about 5. In some embodiments, denaturing the rAAV particles comprises subjecting a composition comprising the rAAV particles to thermal denaturation under conditions that results in a % Fragment DNA content determined using a method disclosed herein that correlates with the % Partial-filled capsid of the same composition determined by AUC. In some embodiments, denaturing the rAAV particles comprises incubating the composition comprising rAAV particles at a temperature that is within 5° C.

of the temperature that results in a % Fragment DNA content determined using a method disclosed herein that correlates with the % Partial-filled capsid of the same composition determined by AUC. In some embodiments, denaturing the rAAV particles comprises incubating the composition comprising rAAV particles at a temperature that is within 10° C. of the temperature that results in a % Fragment DNA content determined using a method disclosed herein that correlates with the % Partial-filled capsid of the same composition determined by AUC. In some embodiments, denaturing the rAAV particles comprises incubating the composition comprising rAAV particles at a temperature that is within 15° C. of the temperature that results in a % Fragment DNA content determined using a method disclosed herein that correlates with the % Partial-filled capsid of the same composition determined by AUC.

In some embodiments, denaturing the rAAV particles comprises incubating the composition comprising rAAV particles at a temperature between about 65° C. and about 95° C. In some embodiments, denaturing the rAAV particles comprises incubating the composition comprising rAAV particles at a temperature between about 65° C. and about 95° C. for between about 5 minutes and 60 minutes. In some embodiments, denaturing the rAAV particles comprises incubating the composition comprising rAAV particles at a temperature between about 65° C. and about 95° C. in the presence of a detergent. In some embodiments, denaturing the rAAV particles comprises incubating the composition comprising rAAV particles at a temperature between about 65° C. and about 95° C. for between about 5 minutes and 60 minutes in the presence of a detergent. In some embodiments, the detergent is SDS. In some embodiments, the detergent is SDS at a concentration between about 0.005% and about 0.5%. In some embodiments, the detergent is SDS at a concentration of about 0.05%. In some embodiments, the detergent is polysorbate 20, polysorbate 80, or Pluronic F-68. In some embodiments, the incubation temperature is between about 70° C. and about 90° C., between about 75° C. and about 85° C., or between about 80° C. and about 85° C. In some embodiments, the incubation temperature is between about 70° C. and about 90° C. In some embodiments, the incubation temperature is between about 75° C. and about 85° C. In some embodiments, the incubation temperature is between about 80° C. and about 85° C.

In some embodiments, denaturing the rAAV particles comprises incubating the composition comprising the rAAV particles at about 70° C., about 75° C., about 80° C., about 85° C., or about 90° C. for between about 5 minutes and 60 minutes. In some embodiments, denaturing the rAAV particles comprises incubating the composition at about 65° C. for between about 5 minutes and 60 minutes. In some embodiments, denaturing the rAAV particles comprises incubating the composition at about 70° C. for between about 5 minutes and 60 minutes. In some embodiments, denaturing the rAAV particles comprises incubating the composition at about 75° C. for between about 5 minutes and 60 minutes. In some embodiments, denaturing the rAAV particles comprises incubating the composition at about 80° C. for between about 5 minutes and 60 minutes. In some embodiments, denaturing the rAAV particles comprises incubating the composition at about 85° C. for between about 5 minutes and 60 minutes. In some embodiments, denaturing the rAAV particles comprises incubating the composition at about 90° C. for between about 5 minutes and 60 minutes. In some embodiments, denaturing the rAAV particles comprises incubating the composition at about 95° C. for between about 5 minutes and 60 minutes. In some embodiments, the composition is incubated for about 5 minutes. In some embodiments, the composition is incubated for about 10 minutes. In some embodiments, the composition is incubated for about 15 minutes. In some embodiments, the composition is incubated for about 20 minutes. In some embodiments, the composition is incubated for about 25 minutes. In some embodiments, the composition is incubated for about 30 minutes. In some embodiments, the composition is incubated for about 35 minutes. In some embodiments, the composition is incubated for about 40 minutes. In some embodiments, the composition is incubated for about 45 minutes. In some embodiments, the composition is incubated for about 50 minutes. In some embodiments, the composition is incubated for about 55 minutes. In some embodiments, the composition is incubated for about 60 minutes. In some embodiments, the composition is incubated in the presence of a detergent. In some embodiments, the composition is incubated in the presence of SDS. In some embodiments, the composition is incubated in the presence of polysorbate 20, polysorbate 80, or Pluronic F-68. In some embodiments, the composition is incubated in the presence of SDS at a concentration between about 0.005% and about 0.5%. In some embodiments, the composition is incubated in the presence of SDS at a concentration of about 0.05%.

In some embodiments, denaturing the rAAV particles comprises exposing the rAAV particles to a detergent. In some embodiments, the detergent is a denaturing detergent. In some embodiments, the detergent is an anionic denaturing detergent. In some embodiments, the detergent is a cationic denaturing detergent. In some embodiments, the detergent is sodium dodecyl sulfate (SDS) or ethyl trimethyl ammonium bromide (ETMAB). In some embodiments, the detergent is sodium dodecyl sulfate (SDS). In some embodiments, denaturing the rAAV particles comprises exposing the rAAV particles to between about 0.005% and about 0.5% of the detergent. In some embodiments, denaturing the rAAV particles comprises exposing the rAAV particles to about 0.05% of the detergent. In some embodiments, denaturing the rAAV particles comprises exposing the rAAV particles to between about 0.005% and about 0.5% of SDS. In some embodiments, denaturing the rAAV particles comprises exposing the rAAV particles to about 0.05% of SDS. In some embodiments, denaturing the rAAV particles comprises exposing the rAAV particles to between about 0.005% and about 0.5% of ETMAB. In some embodiments, denaturing the rAAV particles comprises exposing the rAAV particles to about 0.05% of ETMAB.

In some embodiments, denaturing the rAAV particles comprises exposing the rAAV particles to a detergent. In some embodiments, the detergent is a polysorbate 20, polysorbate 80, or Pluronic® F-68. In some embodiments, denaturing the rAAV particles comprises exposing the rAAV particles to between about 0.005% and about 0.5% of the detergent.

In some embodiments, denaturing the rAAV particles comprises exposing the rAAV particles to a detergent and incubating the composition comprising rAAV particles at a temperature between about 65° C. and about 95° C. In some embodiments, the detergent is sodium dodecyl sulfate (SDS) or ethyl trimethyl ammonium bromide (ETMAB). In some embodiments, the detergent is sodium dodecyl sulfate (SDS). In some embodiments, denaturing the rAAV particles comprises exposing the rAAV particles to between about 0.005% and about 0.5% of the detergent. In some embodiments, denaturing the rAAV particles comprises exposing the rAAV particles to about 0.05% of the detergent. In some embodiments, denaturing the rAAV particles comprises exposing the rAAV particles to between about 0.005% and about 0.5% of SDS. In some embodiments, denaturing the rAAV particles comprises exposing the rAAV particles to about 0.05% of SDS. In some embodiments, denaturing the rAAV particles comprises exposing the rAAV particles to between about 0.005% and about 0.5% of ETMAB. In some embodiments, denaturing the rAAV particles comprises exposing the rAAV particles to about 0.05% of ETMAB. In some embodiments, the incubation temperature is between about 70° C. and about 90° C., between about 75° C. and about 85° C., or between about 80° C. and about 85° C. In some embodiments, the incubation temperature is between about 70° C. and about 90° C. In some embodiments, the incubation temperature is between about 75° C. and about 85° C. In some embodiments, the incubation temperature is between about 80° C. and about 85° C.

In some embodiments, denaturing the rAAV particles comprises exposing the rAAV particles to a chaotropic agent. In some embodiments, the chaotropic agent comprises guanidine hydrochloride, lithium perchlorate, phenol, thiourea, urea, or a combination thereof.

In some embodiments, denaturing the rAAV particles comprises exposing the rAAV particles to a chaotropic agent and incubating the composition comprising rAAV particles at a temperature between about 65° C. and about 95° C. In some embodiments, the chaotropic agent comprises guanidine hydrochloride, lithium perchlorate, phenol, thiourea, urea, or a combination thereof. In some embodiments, the incubation temperature is between about 70° C. and about 90° C., between about 75° C. and about 85° C., or between about 80° C. and about 85° C. In some embodiments, the incubation temperature is between about 70° C. and about 90° C. In some embodiments, the incubation temperature is between about 75° C. and about 85° C. In some embodiments, the incubation temperature is between about 80° C. and about 85° C.

In some embodiments, a method disclosed herein comprises subjecting a composition comprising rAAV particles to a condition under which the rAAV particles are denatured. In some embodiments, substantially all viral particles in the sample are denatured by the denaturation process. In some embodiments, at least about 95%, at least about 97%, at least about 98%, or at least about 99% of the viral particles in the sample are denatured by the denaturation process.

In some embodiments, a method disclosed herein comprises subjecting the composition comprising the denatured rAAV particles to size exclusion chromatography. In some embodiments, the composition comprises denatured capsid polypeptides. In some embodiments, the composition comprises substantially no non-denatured rAAV particles. In some embodiments, less than about 5%, less than about 3%, less than about 2%, or less than about 1% of the capsid polypeptides in the composition are part of a non-denatured rAAV particle.

In some embodiments, a method disclosed herein comprises subjecting the composition comprising the denatured rAAV particles to size exclusion chromatography. In some embodiments, subjecting the composition comprising the denatured rAAV particles to size exclusion chromatography comprises contacting the composition with a size exclusion chromatography resin. Any size exclusion chromatography resin suitable for separating the full length viral genome from viral genome fragments can be used. In some embodiments, the size exclusion chromatography resin comprises silica particles (e.g., Yarra SEC resins and Sepax SRT SEC resins), a cross-linked copolymer of allyl dextran and N,N'- methylene bisacrylamide (e.g., Sephacryl®), or a cross-linked, beaded-form of agarose (e.g., Sepharose®, Superose®, and Superdex®). In some embodiments, the size exclusion chromatography resin comprises silica particles. In some embodiments, the size exclusion chromatography resin comprises uniform, hydrophilic, and neutral nanometer thick films chemically bonded on high purity and enhanced mechanical stability silica. In some embodiments, the size exclusion chromatography resin comprises a nominal pore size between about 50 nm and about 500 nm. In some embodiments, the size exclusion chromatography resin comprises a nominal pore size of about 50 nm. In some embodiments, the size exclusion chromatography resin comprises a nominal pore size of about 100 nm. In some embodiments, the size exclusion chromatography resin comprises a nominal pore size of about 200 nm. In some embodiments, the size exclusion chromatography resin comprises a nominal pore size of about 300 nm. In some embodiments, the size exclusion chromatography resin comprises a nominal pore size of about 400 nm. In some embodiments, the size exclusion chromatography resin comprises a nominal pore size of about 500 nm.

In some embodiments, a method disclosed herein comprises subjecting the composition comprising the denatured rAAV particles to size exclusion chromatography. In some embodiments, the size exclusion chromatography comprises the use of a High Performance Liquid Chromatography or Ultra-High Performance Liquid Chromatography system. In some embodiments, the size exclusion chromatography comprises the use of an Ultra-High Performance Liquid Chromatography system. In some embodiments, the size exclusion chromatography comprises the use of a High Performance Liquid Chromatography system.

In some embodiments, a method disclosed herein comprises subjecting the composition comprising the denatured rAAV particles to size exclusion chromatography, wherein the mobile phase for the size exclusion chromatography comprises one or more of a salt, organic solvent, and detergent. In some embodiments, the mobile phase comprises a salt, organic solvent, and detergent.

In some embodiments, a method disclosed herein comprises subjecting the composition comprising the denatured rAAV particles to size exclusion chromatography, wherein the mobile phase for the size exclusion chromatography comprises one or more of a buffering agent, a salt, organic solvent, and detergent. In some embodiments, the mobile phase comprises a buffering agent, a salt, organic solvent, and detergent.

In some embodiments, the mobile phase comprises a lithium salt, sodium salt, potassium salt, rubidium salt, cesium salt, magnesium salt, or a mixture thereof. In some embodiments, the mobile phase comprises a sodium salt. In some embodiments, the mobile phase comprises sodium citrate, sodium acetate, sodium chloride, or a mixture thereof. In some embodiments, the mobile phase comprises sodium chloride. In some embodiments, the mobile phase comprises sodium chloride, sodium acetate, sodium bicarbonate, sodium carbonate, ammonium carbonate, ammonium chloride, ammonium nitrate, or a mixture thereof.

In some embodiments, the mobile phase comprises between about 100 mM and about 500 mM salt. In some embodiments, the mobile phase comprises between about 100 mM and about 400 mM salt. In some embodiments, the mobile phase comprises between about 200 mM and about 500 mM salt. In some embodiments, the mobile phase comprises between about 200 mM and about 400 mM salt. In some embodiments, the salt comprises a sodium salt. In some embodiments, the salt comprises sodium citrate, sodium acetate, sodium chloride, or a mixture thereof. In some embodiments, the salt comprises sodium chloride.

In some embodiments, the mobile phase comprises about 100 mM, about 150 mM, about 200 mM, about 250 mM, about 300 mM, about 350 mM, about 400 mM, about 450 mM, or about 500 mM salt. In some embodiments, the mobile phase comprises about 100 mM salt. In some embodiments, the mobile phase comprises about 200 mM salt. In some embodiments, the mobile phase comprises about 250 mM salt. In some embodiments, the mobile phase comprises about 300 mM salt. In some embodiments, the mobile phase comprises about 350 mM salt. In some embodiments, the mobile phase comprises about 400 mM salt. In some embodiments, the mobile phase comprises about 500 mM salt. In some embodiments, the salt comprises a sodium salt. In some embodiments, the salt comprises sodium citrate, sodium acetate, sodium chloride, or a mixture thereof. In some embodiments, the salt comprises sodium chloride.

In some embodiments, the mobile phase comprises a buffering agent. Buffering agents are well known in the art, and include without limitation, phosphate buffers, histidine, sodium citrate, HEPES, MES, Tris, Bis-Tris, MOPS, TES, Bicine, glycine, Tricine, N-glycylglycine, sodium acetate, sodium carbonate, glycyl glycine, lysine, arginine, sodium phosphate, and mixtures thereof. In some embodiments, the buffering agent comprises a phosphate buffer. In some embodiment, the buffering agent comprises Tris.

In some embodiments, the mobile phase comprises between about 1 mM and about 50 mM of a buffering agent. In some embodiments, the mobile phase comprises between about 1 mM and about 30 mM, between about 1 mM and about 20 mM, between about 5 mM and about 30 mM, between about 5 mM and about 20 mM, between about 10 mM and about 30 mM, between about 10 mM and about 20 mM, or between about 20 mM and about 50 mM of a buffering agent. In some embodiments, the mobile phase comprises about 1 mM, about 2 mM, about 3 mM, about 5 mM, about 10 mM, about 15 mM, about 20 mM, about 25 mM, about 30 mM, or about 40 mM of a buffering agent. In some embodiments, the mobile phase comprises about 10 mM of a buffering agent. In some embodiments, the buffering agent comprises a phosphate buffer. In some embodiment, the buffering agent comprises Tris.

In some embodiments, the mobile phase comprises between about 1 mM and about 50 mM sodium phosphate. In some embodiments, the mobile phase comprises between about 1 mM and about 30 mM, between about 1 mM and about 20 mM, between about 5 mM and about 30 mM, between about 5 mM and about 20 mM, between about 10 mM and about 30 mM, between about 10 mM and about 20 mM, or between about 20 mM and about 50 mM sodium phosphate. In some embodiments, the mobile phase comprises about 1 mM, about 2 mM, about 3 mM, about 5 mM, about 10 mM, about 15 mM, about 20 mM, about 25 mM, about 30 mM, or about 40 mM sodium phosphate. In some embodiments, the mobile phase comprises about 5 mM sodium phosphate.

In some embodiments, the mobile phase has a pH of between about 6.0 and 8.5. In some embodiments, the mobile phase has a pH of between about 6.0 and 7.0. In some embodiments, the mobile phase has a pH of between about 7.0 and 8.0. In some embodiments, the mobile phase has a pH of between about 8.0 and 8.5. In some embodiments, the mobile phase has a pH of between about 7.2 and 7.8.

In some embodiments, the mobile phase has a pH of about 7.2. In some embodiments, the mobile phase has a pH of about 7.3. In some embodiments, the mobile phase has a pH of about 7.4. In some embodiments, the mobile phase has a pH of about 7.5. In some embodiments, the mobile phase has a pH of about 7.6. In some embodiments, the mobile phase has a pH of about 7.7. In some embodiments, the mobile phase has a pH of about 7.8.

In some embodiments, the mobile phase has a pH of about 7.0. In some embodiments, the mobile phase has a pH of about 7.1. In some embodiments, the mobile phase has a pH of about 7.4. In some embodiments, the mobile phase has a pH of about 7.9. In some embodiments, the mobile phase has a pH of about 8.0.

In some embodiments, the mobile phase has a pH of about 7.5.

In some embodiments, the mobile phase comprises a detergent. In some embodiments, the detergent is a denaturing detergent. In some embodiments, the detergent is a non-denaturing detergent. Acceptable detergents include, without limitations, poloxamer 188, poloxamer 407, polysorbate 80, polysorbate 20, Pluronic F-68, or BRIJ 35. In some embodiments, the mobile phase comprises poloxamer 188, poloxamer 407, polysorbate 80, polysorbate 20, Pluronic F-68, BRIJ 35, or a combination thereof. In some embodiments, the mobile phase comprises polysorbate 80.

In some embodiments, a method disclosed herein comprises denaturing the rAAV particles by a process comprising exposing the rAAV particles to a first detergent, and subjecting the denatured rAAV particles to size exclusion chromatography, wherein the mobile phase for the size exclusion chromatography comprises a second detergent. In some embodiments, a method disclosed herein comprises (a) denaturing the rAAV particles by a process comprising exposing the rAAV particles to a first detergent and incubating the composition comprising rAAV particles at a temperature between about 65° C. and about 95° C., and (b) subjecting the denatured rAAV particles to size exclusion chromatography, wherein the mobile phase for the size exclusion chromatography comprises a second detergent. In some embodiments, the incubation temperature is between about 70° C. and about 90° C., between about 75° C. and about 85° C., or between about 80° C. and about 85° C. In some embodiments, the incubation temperature is between about 70° C. and about 90° C. In some embodiments, the incubation temperature is between about 75° C. and about 85° C. In some embodiments, the incubation temperature is between about 80° C. and about 85° C. In some embodiments, the first and second detergents comprise the same detergent. In some embodiments, the first and second detergents comprise a different detergent. In some embodiments, the first detergent comprises a denaturing detergent and the second detergent comprises a non-denaturing detergent. In some embodiments, the first detergent comprises SDS and the second detergent comprises a non-denaturing detergent. In some embodiments, the first detergent comprises SDS and the second detergent comprises polysorbate 80.

In some embodiments, the mobile phase comprises between about 0.001% and about 5% detergent. In some embodiments, the mobile phase comprises between about 0.05% and about 2% detergent. In some embodiments, the mobile phase comprises between about 0.05% and about 2% detergent. In some embodiments, the mobile phase comprises between about 0.01% and about 1% detergent. In some embodiments, the mobile phase comprises about 0.01%, about 0.05%, about 0.1%, about 0.2%, about 0.3%, about 0.4%, about 0.5%, about 0.6%, about 0.6%, about 0.8%, or about 0.9% detergent. In some embodiments, the detergent comprises polysorbate 80.

In some embodiments, the mobile phase comprises between about 0.001% and about 5% polysorbate 80. In some embodiments, the mobile phase comprises between about 0.05% and about 2% polysorbate 80. In some embodiments, the mobile phase comprises between about 0.05% and about 2% polysorbate 80. In some embodiments, the mobile phase comprises between about 0.01% and about 1% polysorbate 80. In some embodiments, the mobile phase comprises about 0.01%, about 0.05%, about 0.1%, about 0.2%, about 0.3%, about 0.4%, about 0.5%, about 0.6%, about 0.6%, about 0.8%, or about 0.9% polysorbate 80.

In some embodiments, the mobile phase comprises about 0.1% polysorbate 80. In some embodiments, the mobile phase comprises about 0.2% polysorbate 80. In some embodiments, the mobile phase comprises about 0.3% polysorbate 80. In some embodiments, the mobile phase comprises about 0.4% polysorbate 80. In some embodiments, the mobile phase comprises about 0.5% polysorbate 80. In some embodiments, the mobile phase comprises about 0.6% polysorbate 80. In some embodiments, the mobile phase comprises about 0.7% polysorbate 80. In some embodiments, the mobile phase comprises about 0.8% polysorbate 80. In some embodiments, the mobile phase comprises about 0.9% polysorbate 80.

In some embodiments, the mobile phase comprises an organic solvent. Acceptable organic solvents include, without limitations, methanol, isopropanol, acetonitrile, dimethyl sulfoxide (DMSO), tetrahydrofuran (THF), trifluoroethanol (TFE), hexafluoroisopropanol (HFIP), or a combination thereof. In some embodiments, the mobile phase comprises methanol.

In some embodiments, the mobile phase comprises between about 5% and about 50% organic solvent. In some embodiments, the mobile phase comprises between about 10% and about 40% organic solvent. In some embodiments, the mobile phase comprises between about 10% and about 30% organic solvent. In some embodiments, the mobile phase comprises between about 10% and about 50% organic solvent. In some embodiments, the mobile phase comprises between about 5% and about 20% organic solvent. In some embodiments, the mobile phase comprises between about 20% and about 50% organic solvent. In some embodiments, the mobile phase comprises between about 20% and about 40% organic solvent. In some embodiments, the mobile phase comprises about 5%, about 10%, about 15%, about 20%, about 25%, about 30%, about 35%, about 40%, about 45%, or about 50% organic solvent. In some embodiments, the organic solvent comprises methanol.

In some embodiments, the mobile phase comprises between about 5% and about 50% methanol. In some embodiments, the mobile phase comprises between about 10% and about 40% methanol. In some embodiments, the mobile phase comprises between about 10% and about 30% methanol. In some embodiments, the mobile phase comprises between about 10% and about 50% methanol. In some embodiments, the mobile phase comprises between about 5% and about 20% methanol. In some embodiments, the mobile phase comprises between about 20% and about 50% methanol. In some embodiments, the mobile phase comprises between about 20% and about 40% methanol. In some embodiments, the mobile phase comprises about 5%, about 10%, about 15%, about 20%, about 25%, about 30%, about 35%, about 40%, about 45%, or about 50% methanol.

In some embodiments, the mobile phase comprises about 10% methanol. In some embodiments, the mobile phase comprises about 15% methanol. In some embodiments, the mobile phase comprises about 20% methanol. In some embodiments, the mobile phase comprises about 25% methanol. In some embodiments, the mobile phase comprises about 30% methanol. In some embodiments, the mobile phase comprises about 35% methanol. In some embodiments, the mobile phase comprises about 40% methanol.

In some embodiments, the mobile phase comprises between about 5 mM and about 50 mM sodium phosphate, between about 100 mM and about 500 mM sodium chloride, between about 0.01% and about 0.5% polysorbate 80, and between about 5% and about 50% methanol and has a pH between about 6.5 and 8.5.

In some embodiments, the mobile phase comprises about 10 mM sodium phosphate, about 300 mM sodium chloride, about 0.05% polysorbate 80, and about 20% methanol and has a pH of about 7.5.

In some embodiments, a disclosed herein comprises (a) subjecting a composition comprising rAAV particles to a condition under which the rAAV particles are denatured; and (b) subjecting the composition comprising the denatured rAAV particles to size exclusion chromatography. In some embodiments, the composition comprising rAAV particles comprises between about 2E+10 genome copy/ml and about 1E+14 genome copy/ml rAAV particles. In some embodiments, the composition comprises about 2.0E+10 GC/mL, about 1.0E+11 GC/mL, about 1.0E+12 GC/mL, about 1.0E+13 GC/mL, or about 1.0E+14 GC/mL rAAV particles. In some embodiments, the composition comprises rAAV particles comprising a capsid protein of the AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 serotype, or a combination thereof. In some embodiments, the composition comprises rAAV particles comprising a capsid protein of the AAV-8 serotype, AAV-9 serotype, or a combination thereof.

The methods disclosed herein can be applied to rAAV particles comprising a capsid protein from any AAV capsid serotype. In some embodiments, the rAAV particles comprise a capsid protein from an AAV capsid serotype selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise a capsid protein that is a derivative, modification, or pseudotype of AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 capsid protein.

In some embodiments, the rAAV particles comprise a capsid protein from an AAV capsid serotype selected from AAV-8 and AAV-9. In some embodiments, the rAAV particles have an AAV capsid serotype of AAV-8. In some embodiments, the rAAV particles have an AAV capsid serotype of AAV-9.

In some embodiments, the rAAV particles comprise a capsid protein that is a derivative, modification, or pseudotype of AAV-8 or AAV-9 capsid protein. In some embodiments, the rAAV particles comprise a capsid protein that has an AAV-8 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV-8 capsid protein.

In some embodiments, the rAAV particles comprise a capsid protein that is a derivative, modification, or pseudotype of AAV-9 capsid protein. In some embodiments, rAAV particles in the feed composition comprise a capsid protein that has an AAV-9 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV-9 capsid protein.

In additional embodiments, the rAAV particles comprise a mosaic capsid. In additional embodiments, the rAAV particles comprise a pseudotyped rAAV particle. In additional embodiments, the rAAV particles comprise a capsid containing a capsid protein chimera of two or more AAV capsid serotypes.

In some embodiments, a method disclosed herein comprises determining vector genome size purity, assessing the folding or secondary structure of vector genomes inside the capsids, and/or vector genome titer (Vg) of the composition comprising rAAV particles. Methods for determining these characteristics of a composition comprising rAAV particles from the UV absorbance readings obtained using a method disclosed herein are known to the skilled artisan, for example, as disclosed in WO 2019/212922, which is incorporated herein by reference in its entirety.

In some embodiments, a method disclosed herein is used to support product development and process optimization by rapidly assessing the quality of rAAV particles produced by the modified processes. In some embodiments, a method disclosed herein comprises determining effect of a process modification on the quality of rAAV particles produced by the modified process. In some embodiments, the quality of rAAV particles is assessed by determining the % of fragmented DNA in the rAAV particles.

In some embodiments, a method disclosed herein is used to assess the quality of rAAV particles at different stages of an rAAV manufacturing process. For example, a method disclosed herein can be used to assess the quality of rAAV particles following harvest of a cell culture, clarification of the harvested cell culture (e.g., by centrifugation or depth filtration), tangential flow filtration, affinity chromatography, anion exchange chromatography, cation exchange chromatography, size exclusion chromatography, hydrophobic interaction chromatography, and sterile filtration. In some embodiments, assessing the quality of the rAAV particles comprises determining % fragmented DNA content of the particles. In some embodiments, a method disclosed herein is suitable for batch release, e.g. for batch release testing and/or lot release testing. In some embodiments, a method disclosed herein is performed as part of lot release testing.

rAAV Particles

The provided methods are suitable to characterize any isolated recombinant AAV particles, including but not limited to determining the vector genome size purity of a composition comprising any isolated rAAV particles, assessing the folding or secondary structure of vector genomes inside the capsids, and determining vector genome titer (Vg) of a composition comprising any isolated rAAV particles. Additionally, the provided methods are suitable to isolate AAV genome from any isolated recombinant AAV particles. As such, the rAAV can be of any serotype, modification, or derivative, known in the art, or any combination thereof (e.g., a population of rAAV particles that comprises two or more serotypes, e.g., comprising two or more of rAAV2, rAAV8, and rAAV9 particles) known in the art. In some embodiments, the rAAV particles are AAV1, AAV2, rAAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or other rAAV particles, or combinations of two or more thereof.

In some embodiments, rAAV particles have a capsid protein from an AAV serotype selected from AAV1, AAV1, AAV2, rAAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2YF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or a derivative, modification, or pseudotype thereof. In some embodiments, rAAV particles comprise a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to e.g., VP1, VP2 and/or VP3 sequence of an AAV capsid serotype selected from AAV1, AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, rAAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In some embodiments, rAAV particles comprise a capsid protein from an AAV capsid serotype selected from AAV1, AAV1, AAV2, rAAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16, or a derivative, modification, or pseudotype thereof. In some embodiments, rAAV particles comprise a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to e.g., VP1, VP2 and/or VP3 sequence of an AAV capsid serotype selected from AAV1, AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In some embodiments, rAAV particles comprise the capsid of Anc80 or Anc80L65, as described in Zinn et al., 2015, Cell Rep. 12 (6): 1056-1068, which is incorporated by reference in its entirety. In certain embodiments, the rAAV particles comprise the capsid with one of the following amino acid insertions: LGETTRP (SEQ ID NO: 1) or LALGETTRP (SEQ ID NO: 2), as described in U.S. Pat. Nos. 9,193,956; 9,458,517; and 9,587,282 and US patent application publication no. 2016/0376323, each of which is incorporated herein by reference in its entirety. In some embodiments, rAAV particles comprise the capsid of AAV.7m8, as described in U.S. Pat. Nos. 9,193,956; 9,458, 517; and 9,587,282 and US patent application publication no. 2016/0376323, each of which is incorporated herein by reference in its entirety. In some embodiments, rAAV particles comprise any AAV capsid disclosed in U.S. Pat. No. 9,585,971, such as AAV-PHP.B. In some embodiments, rAAV particles comprise any AAV capsid disclosed in U.S. Pat. No. 9,840,719 and WO 2015/013313, such as AAV.Rh74 and RHM4-1, each of which is incorporated herein by reference in its entirety. In some embodiments, rAAV particles comprise any AAV capsid disclosed in WO 2014/172669, such as AAV rh.74, which is incorporated herein by reference in its entirety. In some embodiments, rAAV particles comprise the capsid of AAV2/5, as described in Georgiadis et al., 2016, Gene Therapy 23:857-862 and Georgiadis et al., 2018, Gene Therapy 25:450, each of which is incorporated by reference in its entirety. In some embodiments, rAAV particles comprise any AAV capsid disclosed in WO 2017/070491, such as AAV2tYF, which is incorporated herein by reference in its entirety. In some embodiments, rAAV particles comprise the capsids of AAVLK03 or AAV3B, as described in Puzzo et al., 2017, Sci. Transl. Med. 29 (9): 418, which is incorporated by reference in its entirety. In some embodiments, rAAV particles comprise any AAV capsid disclosed in U.S. Pat. Nos. 8,628,966; 8,927,514; 9,923,120 and WO 2016/049230, such as HSC1, HSC2, HSC3, HSC4, HSC5, HSC6, HSC7, HSC8, HSC9, HSC10, HSC11, HSC12, HSC13, HSC14, HSC15, or HSC16, each of which is incorporated by reference in its entirety.

In some embodiments, rAAV particles comprise an AAV capsid disclosed in any of the following patents and patent applications, each of which is incorporated herein by reference in its entirety: U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/ 0374803; 2015/0126588; 2017/0067908; 2013/0224836;

2016/0215024; 2017/0051257; and International Patent Application Nos. PCT/US2015/034799; PCT/EP2015/053335. In some embodiments, rAAV particles have a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of an AAV capsid disclosed in any of the following patents and patent applications, each of which is incorporated herein by reference in its entirety: U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; and International Patent Application Nos. PCT/US2015/034799; PCT/EP2015/053335.

In some embodiments, rAAV particles have a capsid protein disclosed in Intl. Appl. Publ. No. WO 2003/052051 (see, e.g., SEQ ID NO: 2), WO 2005/033321 (see, e.g., SEQ ID NOs: 123 and 88), WO 03/042397 (see, e.g., SEQ ID NOs: 2, 81, 85, and 97), WO 2006/068888 (see, e.g., SEQ ID NOs: 1 and 3-6), WO 2006/110689, (see, e.g., SEQ ID NOs: 5-38) WO2009/104964 (see, e.g., SEQ ID NOs: 1-5, 7, 9, 20, 22, 24 and 31), WO 2010/127097 (see, e.g., SEQ ID NOs: 5-38), and WO 2015/191508 (see, e.g., SEQ ID NOs: 80-294), and U.S. Appl. Publ. No. 20150023924 (see, e.g., SEQ ID NOs: 1, 5-10), the contents of each of which is herein incorporated by reference in its entirety. In some embodiments, rAAV particles have a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of an AAV capsid disclosed in Intl. Appl. Publ. No. WO 2003/052051 (see, e.g., SEQ ID NO: 2), WO 2005/033321 (see, e.g., SEQ ID NOs: 123 and 88), WO 03/042397 (see, e.g., SEQ ID NOs: 2, 81, 85, and 97), WO 2006/068888 (see, e.g., SEQ ID NOs: 1 and 3-6), WO 2006/110689 (see, e.g., SEQ ID NOs: 5-38) WO2009/104964 (see, e.g., SEQ ID NOs: 1-5, 7, 9, 20, 22, 24 and 31), WO 2010/127097 (see, e.g., SEQ ID NOs: 5-38), and WO 2015/191508 (see, e.g., SEQ ID NOs: 80-294), and U.S. Appl. Publ. No. 20150023924 (see, e.g., SEQ ID NOs: 1, 5-10).

Nucleic acid sequences of AAV based viral vectors and methods of making recombinant AAV and AAV capsids are taught, for example, in U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; International Patent Application Nos. PCT/US2015/034799; PCT/EP2015/053335; WO 2003/052051, WO 2005/033321, WO 03/042397, WO 2006/068888, WO 2006/110689, WO2009/104964, WO 2010/127097, and WO 2015/191508, and U.S. Appl. Publ. No. 20150023924.

The provided methods are suitable for used in the production of recombinant AAV encoding a transgene. In some embodiments, provided herein are rAAV viral vectors encoding an anti-VEGF Fab. In specific embodiments, provided herein are rAAV8-based viral vectors encoding an anti-VEGF Fab. In more specific embodiments, provided herein are rAAV8-based viral vectors encoding ranibizumab. In some embodiments, provided herein are rAAV viral vectors encoding Iduronidase (IDUA). In specific embodiments, provided herein are rAAV9-based viral vectors encoding IDUA. In some embodiments, provided herein are rAAV viral vectors encoding Iduronate 2-Sulfatase (IDS). In specific embodiments, provided herein are rAAV9-based viral vectors encoding IDS. In some embodiments, provided herein are rAAV viral vectors encoding a low-density lipoprotein receptor (LDLR). In specific embodiments, provided herein are rAAV8-based viral vectors encoding LDLR. In some embodiments, provided herein are rAAV viral vectors encoding tripeptidyl peptidase 1 (TPP1) protein. In specific embodiments, provided herein are rAAV9-based viral vectors encoding TPP.

In additional embodiments, rAAV particles comprise a pseudotyped AAV capsid. In some embodiments, the pseudotyped AAV capsids are rAAV2/8 or rAAV2/9 pseudotyped AAV capsids. Methods for producing and using pseudotyped rAAV particles are known in the art (see, e.g., Duan et al., J. Virol., 75:7662-7671 (2001); Halbert et al., J. Virol., 74:1524-1532 (2000); Zolotukhin et al., Methods 28:158-167 (2002); and Auricchio et al., Hum. Molec. Genet. 10:3075-3081, (2001).

In additional embodiments, rAAV particles comprise a capsid containing a capsid protein chimeric of two or more AAV capsid serotypes. In some embodiments, the capsid protein is a chimeric of 2 or more AAV capsid proteins from AAV serotypes selected from AAV1, AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In certain embodiments, a single-stranded AAV (ssAAV) can be used. In certain embodiments, a self-complementary vector, e.g., scAAV, can be used (see, e.g., Wu, 2007, Human Gene Therapy, 18 (2): 171-82, McCarty et al, 2001, Gene Therapy, Vol. 8, Number 16, Pages 1248-1254; and U.S. Pat. Nos. 6,596,535; 7,125,717; and 7,456,683, each of which is incorporated herein by reference in its entirety).

In some embodiments, the rAAV particles comprise a capsid protein from an AAV capsid serotype selected from AAV-8 or AAV-9. In some embodiments, the rAAV particles have an AAV capsid serotype of AAV-8. In some embodiments, the rAAV particles have an AAV capsid serotype of AAV-9.

In some embodiments, the rAAV particles comprise a capsid protein that is a derivative, modification, or pseudo-type of AAV-8 or AAV-9 capsid protein. In some embodiments, the rAAV particles comprise a capsid protein that has an AAV-8 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV-8 capsid protein.

In some embodiments, the rAAV particles comprise a capsid protein that is a derivative, modification, or pseudo-type of AAV-9 capsid protein. In some embodiments, the rAAV particles comprise a capsid protein that has an AAV-9 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV-9 capsid protein.

In additional embodiments, the rAAV particles comprise a mosaic capsid. Mosaic AAV particles are composed of a mixture of viral capsid proteins from different serotypes of AAV. In some embodiments, the rAAV particles comprise a mosaic capsid containing capsid proteins of a serotype selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise a mosaic capsid containing capsid proteins of a serotype selected from AAV-1, AAV-2, AAV-5, AAV-6, AAV-7, AAV-8, AAV-9, AAV-10, AAVrh.8, AAVrh.10, AAVhu.37, AAVrh.20, and AAVrh.74.

In additional embodiments, the rAAV particles comprise a pseudotyped rAAV particle. In some embodiments, the pseudotyped rAAV particle comprises (a) a nucleic acid vector comprising AAV ITRs and (b) a capsid comprised of capsid proteins derived from AAVx (e.g., AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16). In additional embodiments, the rAAV particles comprise a pseudotyped rAAV particle comprised of a capsid protein of an AAV serotype selected from AAV-1, AAV-2, AAV-5, AAV-6, AAV-7, AAV-8, AAV-9, AAV-10, AAVrh.8, and AAVrh.10, AAVhu.37, AAVrh.20, and AAVrh.74. In additional embodiments, the rAAV particles comprise a pseudotyped rAAV particle containing AAV-8 capsid protein. In additional embodiments, the rAAV particles comprise a pseudotyped rAAV particle is comprised of AAV-9 capsid protein. In some embodiments, the pseudotyped rAAV8 or rAAV9 particles are rAAV2/8 or rAAV2/9 pseudotyped particles. Methods for producing and using pseudotyped rAAV particles are known in the art (see, e.g., Duan et al., J. Virol., 75:7662-7671 (2001); Halbert et al., J. Virol., 74:1524-1532 (2000); Zolotukhin et al., Methods 28:158-167 (2002); and Auricchio et al., Hum. Molec. Genet. 10:3075-3081, (2001).

In additional embodiments, the rAAV particles comprise a capsid containing a capsid protein chimeric of two or more AAV capsid serotypes. In some embodiments, the rAAV particles comprise an AAV capsid protein chimeric of AAV-8 capsid protein and one or more AAV capsid proteins from an AAV serotype selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise an AAV capsid protein chimeric of AAV-8 capsid protein and one or more AAV capsid proteins from an AAV serotype selected from AAV-1, AAV-2, AAV-5, AAV-6, AAV-7, AAV-9, AAV-10, rAAVrh10, AAVrh.8, AAVrh.10, AAVhu.37, AAVrh.20, and AAVrh.74. In some embodiments, the rAAV particles comprise an AAV capsid protein chimeric of AAV-9 capsid protein the capsid protein of one or more AAV capsid serotypes selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise an AAV capsid protein chimeric of AAV-9 capsid protein the capsid protein of one or more AAV capsid serotypes selected from AAV1, AAV2, AAV3, AAV4, AAV5, AA6, AAV7, AAV8, AAV9, AAVrh.8, AAVrh. 10, AAVhu.37, AAVrh.20, and AAVrh.74.

Methods for Isolating rAAV Particles

In some embodiments, the disclosure provides methods for producing a composition comprising isolated recombinant adeno-associated virus (rAAV) particles, comprising (a) isolating rAAV particles from a feed comprising an impurity (for example, rAAV production culture), and (b) characterizing the isolated rAAV particles using a method disclosed herein. In some embodiments, a method for producing a formulation comprising isolated recombinant adeno-associated virus (rAAV) particles disclosed herein comprises (a) isolating rAAV particles from a feed comprising an impurity (for example, rAAV production culture), (b) characterizing the isolated rAAV particles using a method disclosed herein, and (c) formulating the isolated rAAV particles to produce the formulation.

In some embodiments, the disclosure further provides methods for producing a pharmaceutical unit dosage of a formulation comprising isolated recombinant adeno-associated virus (rAAV) particles, comprising isolating rAAV particles from a feed comprising an impurity (for example, rAAV production culture), characterizing the isolated rAAV particles using a method disclosed herein, and formulating the isolated rAAV particles.

Isolated rAAV particles can be isolated using methods known in the art. In some embodiments, methods of isolating rAAV particles comprises downstream processing such as, for example, harvest of a cell culture, clarification of the harvested cell culture (e.g., by centrifugation or depth filtration), tangential flow filtration, affinity chromatography, anion exchange chromatography, cation exchange chromatography, size exclusion chromatography, hydrophobic interaction chromatography, hydroxylapatite chromatography, sterile filtration, or any combination(s) thereof. In some embodiments, downstream processing includes at least 2, at least 3, at least 4, at least 5 or at least 6 of: harvest of a cell culture, clarification of the harvested cell culture (e.g., by centrifugation or depth filtration), tangential flow filtration, affinity chromatography, anion exchange chromatography, cation exchange chromatography, size exclusion chromatography, hydrophobic interaction chromatography, hydroxylapatite chromatography, and sterile filtration. In some embodiments, downstream processing comprises harvest of a cell culture, clarification of the harvested cell culture (e.g., by depth filtration), sterile filtration, tangential flow filtration, affinity chromatography, and anion exchange chromatography. In some embodiments, downstream processing comprises clarification of a harvested cell culture, sterile filtration, tangential flow filtration, affinity chromatography, and anion exchange chromatography. In some embodiments, downstream processing comprises clarification of a harvested cell culture by depth filtration, sterile filtration, tangential flow filtration, affinity chromatography, and anion exchange chromatography. In some embodiments, clarification of the harvested cell culture comprises sterile filtration. In some embodiments, downstream processing does not include centrifugation. In some embodiments, the rAAV particles comprise a capsid protein of the AAV-8 serotype. In some embodiments, the rAAV particles comprise a capsid protein of the AAV-9 serotype.

In some embodiments, a method of isolating rAAV particles comprises harvest of a cell culture, clarification of the harvested cell culture (e.g., by depth filtration), a first sterile filtration, a first tangential flow filtration, affinity chromatography, monolith anion exchange chromatography, a second tangential flow filtration, and a second sterile filtration. In some embodiments, a method of isolating rAAV particles comprises clarification of a harvested cell culture, a first sterile filtration, a first tangential flow filtration, affinity chromatography, monolith anion exchange chromatography, a second tangential flow filtration, and a second sterile filtration. In some embodiments, a method of isolating rAAV particles comprises clarification of a harvested cell culture by depth filtration, a first sterile filtration, a first tangential flow filtration, affinity chromatography, monolith anion exchange chromatography, a second tangential flow filtration, and a second sterile filtration. In some embodiments, the method does not include centrifugation. In some embodiments, clarification of the harvested cell culture comprises sterile filtration. In some embodiments, the rAAV particles comprise a capsid protein of the AAV-8 serotype. In some embodiments, the rAAV particles comprise a capsid protein of the AAV-9 serotype.

Numerous methods are known in the art for production of rAAV particles, including transfection, stable cell line production, and infectious hybrid virus production systems which include adenovirus-AAV hybrids, herpesvirus-AAV hybrids and baculovirus-AAV hybrids. rAAV production cultures for the production of rAAV virus particles all require; (1) suitable host cells, including, for example, human-derived cell lines such as HeLa, A549, or HEK293 cells and their derivatives (HEK293T cells, HEK293F cells), mammalian cell lines such as Vero, or insect-derived cell lines such as SF-9 in the case of baculovirus production systems; (2) suitable helper virus function, provided by wild type or mutant adenovirus (such as temperature sensitive adenovirus), herpes virus, baculovirus, or a plasmid construct providing helper functions; (3) AAV rep and cap genes and gene products; (4) a transgene (such as a therapeutic transgene) flanked by AAV ITR sequences; and (5) suitable media and media components to support rAAV production. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), and Sf-900 II SFM media as described in U.S. Pat. No. 6,723,551, which is incorporated herein by reference in its entirety.

rAAV production cultures can routinely be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, microcarriers, and packed-bed or fluidized-bed bioreactors. rAAV vector production cultures may also include suspension-adapted host cells such as HeLa, HEK293, Vero, and its derivatives, and SF-9 cells which can be cultured in a variety of ways including, for example, spinner flasks, stirred tank bioreactors, and disposable systems such as the Wave bag system. Numerous suspension cultures are known in the art for production of rAAV particles, including for example, the cultures disclosed in U.S. Pat. Nos. 6,995,006, 9,783,826, and in U.S. Pat. Appl. Pub. No. 20120122155, each of which is incorporated herein by reference in its entirety.

In some embodiments, methods for the production of rAAV particles encompasses providing a cell culture comprising a cell capable of producing rAAV; adding to the cell culture a histone deacetylase (HDAC) inhibitor to a final concentration between about 0.1 mM and about 20 mM; and maintaining the cell culture under conditions that allows production of the rAAV particles. In some embodiments, the HDAC inhibitor comprises a short-chain fatty acid or salt thereof. In some embodiments, the HDAC inhibitor comprises butyrate (e.g., sodium butyrate), valproate (e.g., sodium valproate), propionate (e.g., sodium propionate), or a combination thereof.

In some embodiments, rAAV particles are produced as disclosed in WO 2020/033842, which is incorporated herein by reference in its entirety.

Recombinant AAV particles can be harvested from rAAV production cultures by harvest of the production culture comprising host cells or by harvest of the spent media from the production culture, provided the cells are cultured under conditions known in the art to cause release of rAAV particles into the media from intact host cells. Recombinant AAV particles can also be harvested from rAAV production cultures by lysis of the host cells of the production culture. Suitable methods of lysing cells are also known in the art and include for example multiple freeze/thaw cycles, sonication, microfluidization, and treatment with chemicals, such as detergents and/or proteases.

At harvest, rAAV production cultures can contain one or more of the following: (1) host cell proteins; (2) host cell DNA; (3) plasmid DNA; (4) helper virus; (5) helper virus proteins; (6) helper virus DNA; and (7) media components including, for example, serum proteins, amino acids, transferrins and other low molecular weight proteins. rAAV production cultures can further contain product-related impurities, for example, inactive vector forms, empty viral capsids, aggregated viral particles or capsids, mis-folded viral capsids, degraded viral particle.

In some embodiments, the rAAV production culture harvest is clarified to remove host cell debris. In some embodiments, the production culture harvest is clarified by filtration through a series of depth filters. Clarification can also be achieved by a variety of other standard techniques known in the art, such as, centrifugation or filtration through any cellulose acetate filter of 0.2 mm or greater pore size known in the art. In some embodiments, clarification of the harvested cell culture comprises sterile filtration. In some embodiments, the production culture harvest is clarified by centrifugation. In some embodiments, clarification of the production culture harvest does not included centrifugation.

In some embodiments, harvested cell culture is clarified using filtration. In some embodiments, clarification of the harvested cell culture comprises depth filtration. In some embodiments, clarification of the harvested cell culture further comprises depth filtration and sterile filtration. In some embodiments, harvested cell culture is clarified using a filter train comprising one or more different filtration media. In some embodiments, the filter train comprises a depth filtration media. In some embodiments, the filter train comprises one or more depth filtration media. In some embodiments, the filter train comprises two depth filtration media. In some embodiments, the filter train comprises a sterile filtration media. In some embodiments, the filter train comprises 2 depth filtration media and a sterile filtration media. In some embodiments, the depth filter media is a porous depth filter. In some embodiments, the filter train comprises Clarisolve® 20 MS, Millistak+® COHC, and a sterilizing grade filter media. In some embodiments, the filter train comprises Clarisolve® 20 MS, Millistak+® COHC, and Sartopore® 2 XLG 0.2 μm. In some embodiments, the harvested cell culture is pretreated before contacting it with the depth filter. In some embodiments, the pretreating comprises adding a salt to the harvested cell culture. In some embodiments, the pretreating comprises adding a chemical flocculent to the harvested cell culture. In some embodiments, the harvested cell culture is not pretreated before contacting it with the depth filter.

In some embodiments, the production culture harvest is clarified by filtration are disclosed in WO 2019/212921, which is incorporated herein by reference in its entirety.

In some embodiments, the rAAV production culture harvest is treated with a nuclease (e.g., Benzonase®) or endonuclease (e.g., endonuclease from *Serratia marcescens*) to digest high molecular weight DNA present in the production culture. The nuclease or endonuclease digestion can routinely be performed under standard conditions known in the art. For example, nuclease digestion is performed at a final concentration of 1-2.5 units/ml of Benzonase® at a temperature ranging from ambient to 37° C. for a period of 30 minutes to several hours.

Sterile filtration encompasses filtration using a sterilizing grade filter media. In some embodiments, the sterilizing grade filter media is a 0.2 or 0.22 μm pore filter. In some embodiments, the sterilizing grade filter media comprises polyethersulfone (PES). In some embodiments, the sterilizing grade filter media comprises polyvinylidene fluoride (PVDF). In some embodiments, the sterilizing grade filter media has a hydrophilic heterogeneous double layer design. In some embodiments, the sterilizing grade filter media has a hydrophilic heterogeneous double layer design of a 0.8 μm pre-filter and 0.2 μm final filter membrane. In some embodiments, the sterilizing grade filter media has a hydrophilic heterogeneous double layer design of a 1.2 μm pre-filter and 0.2 μm final filter membrane. In some embodiments, the sterilizing grade filter media is a 0.2 or 0.22 μm pore filter. In further embodiments, the sterilizing grade filter media is a 0.2 μm pore filter. In some embodiments, the sterilizing grade filter media is a Sartopore® 2 XLG 0.2 μm, Durapore™ PVDF Membranes 0.45 μm, or Sartoguard® PES 1.2 μm+0.2 μm nominal pore size combination. In some embodiments, the sterilizing grade filter media is a Sartopore® 2 XLG 0.2 μm.

In some embodiments, the clarified feed is concentrated via tangential flow filtration ("TFF") before being applied to a chromatographic medium, for example, affinity chromatography medium. Large scale concentration of viruses using TFF ultrafiltration has been described by Paul et al., Human Gene Therapy 4:609-615 (1993). TFF concentration of the clarified feed enables a technically manageable volume of clarified feed to be subjected to chromatography and allows for more reasonable sizing of columns without the need for lengthy recirculation times. In some embodiments, the clarified feed is concentrated between at least two-fold and at least ten-fold. In some embodiments, the clarified feed is concentrated between at least ten-fold and at least twenty-fold. In some embodiments, the clarified feed is concentrated between at least twenty-fold and at least fifty-fold. In some embodiments, the clarified feed is concentrated between at least twenty-fold and at least fifty-fold. In some embodiments, the clarified feed is concentrated about twenty-fold. One of ordinary skill in the art will also recognize that TFF can also be used to remove small molecule impurities (e.g., cell culture contaminants comprising media components, serum albumin, or other serum proteins) form the clarified feed via diafiltration. In some embodiments, the clarified feed is subjected to diafiltration to remove small molecule impurities. In some embodiments, the diafiltration comprises the use of between about 3 and about 10 diafiltration volume of buffer. In some embodiments, the diafiltration comprises the use of about 5 diafiltration volume of buffer. One of ordinary skill in the art will also recognize that TFF can also be used at any step in the purification process where it is desirable to exchange buffers before performing the next step in the purification process. In some embodiments, the methods for isolating rAAV from the clarified feed disclosed herein comprise the use of TFF to exchange buffers.

Affinity chromatography can be used to isolate rAAV particles from a composition. In some embodiments, affinity chromatography is used to isolate rAAV particles from the clarified feed. In some embodiments, affinity chromatography is used to isolate rAAV particles from the clarified feed that has been subjected to tangential flow filtration. Suitable affinity chromatography media are known in the art and include without limitation, AVB Sepharose™, POROS™ CaptureSelect™ AAVX affinity resin, POROS™ CaptureSelect™ AAV9 affinity resin, and POROS™ CaptureSelect™ AAV8 affinity resin. In some embodiments, the affinity chromatography media is POROS™ CaptureSelect™ AAV9 affinity resin. In some embodiments, the affinity chromatography media is POROS™ CaptureSelect™ AAV8 affinity resin. In some embodiments, the affinity chromatography media is POROS™ CaptureSelect™ AAVX affinity resin.

Anion exchange chromatography can be used to isolate rAAV particles from a composition. In some embodiments, anion exchange chromatography is used after affinity chromatography as a final concentration and polish step. Suitable anion exchange chromatography media are known in the art and include without limitation, Unosphere Q (Biorad, Hercules, Calif.), and N-charged amino or imino resins such as e.g., POROS 50 PI, or any DEAE, TMAE, tertiary or quaternary amine, or PEI-based resins known in the art (U.S. Pat. No. 6,989,264; Brument et al., Mol. Therapy 6 (5): 678-686 (2002); Gao et al., Hum. Gene Therapy 11:2079-2091 (2000)). In some embodiments, the anion exchange chromatography media comprises a quaternary amine. In some embodiments, the anion exchange media is a monolith anion exchange chromatography resin. In some embodiments, the monolith anion exchange chromatography media comprises glycidylmethacrylate-ethylenedimethacrylate or styrene-divinylbenzene polymers. In some embodiments, the monolith anion exchange chromatography media is selected from the group consisting of CIMmultus™ QA-1 Advanced Composite Column (Quaternary amine), CIMmultus™ DEAE-1 Advanced Composite Column (Diethylamino), CIM® QA Disk (Quaternary amine), CIM® DEAE, and CIM® EDA Disk (Ethylene diamino). In some embodiments, the monolith anion exchange chromatography media is CIMmultus™ QA-1 Advanced Composite Column (Quaternary amine). In some embodiments, the monolith anion exchange chromatography media is CIM® QA Disk (Quaternary amine). In some embodiments, the anion exchange chromatography media is CIM QA (BIA Separations, Slovenia). In some embodiments, the anion exchange chromatography media is BIA CIM® QA-80 (Column volume is 80 mL). One of ordinary skill in the art can appreciate that wash buffers of suitable ionic strength can be identified such that the rAAV remains bound to the resin while impurities, including without limitation impurities which may be introduced by upstream purification steps are stripped away.

In some embodiments, anion exchange chromatography is performed according to a method disclosed in WO 2019/241535, which is incorporated herein by reference in its entirety.

In some embodiments, a method of isolating rAAV particles comprises determining the vector genome titer, capsid titer, and/or the ratio of full to empty capsids in a composition comprising the isolated rAAV particles. In some embodiments, the vector genome titer is determined by quantitative PCR (qPCR) or digital PCR (dPCR) or droplet digital PCR (ddPCR). In some embodiments, the capsid titer is determined by serotype-specific ELISA. In some embodiments, the ratio of full to empty capsids is determined by Analytical Ultracentrifugation (AUC) or Transmission Electron Microscopy (TEM).

In some embodiments, the vector genome titer, capsid titer, and/or the ratio of full to empty capsids is determined by spectrophotometry, for example, by measuring the absorbance of the composition at 260 nm; and measuring the absorbance of the composition at 280 nm. In some embodiments, the rAAV particles are not denatured prior to measuring the absorbance of the composition. In some embodiments, the rAAV particles are denatured prior to measuring the absorbance of the composition. In some embodiments, the absorbance of the composition at 260 nm and 280 nm is determined using a spectrophotometer. In some embodiments, the absorbance of the composition at 260 nm and 280 nm is determined using a HPLC. In some embodiments, the absorbance is peak absorbance. Several methods for measuring the absorbance of a composition at 260 nm and 280 nm are known in the art. Methods of determining vector genome titer and capsid titer of a composition comprising the isolated recombinant rAAV particles are disclosed in WO 2019/212922, which is incorporated herein by reference in its entirety.

EXAMPLES

Example 1. Assessing Purity and Structures of AAV Vector Genomes by High Performance Size Exclusion Chromatography Product purity is a critical quality attribute for therapeutic biologics with the potential to impact safety and efficacy, thus assurance of control, including release testing, is critical. The AAV vector genome is delivered to the cell nucleus and can be persistent for a long period, much longer than capsid proteins. Thus, it is desirable to assess the vector genome purity for AAV products. The relative purity of intact AAV that quantify the empty and full capsid ratio can be determined by Analytical Ultracentrifugation (AUC), cryo-electron microscopy, and ion-exchange chromatography. In addition, the presence of vectors with fragmented genomes and non-transgene-related DNA contaminants, often referred to as partially-filled capsids, can be resolved by AUC. Capsid protein purity can be determined by SDS-PAGE or SDS-CGE. While a few studies have been published to analyze AAV genome by capillary and gel electrophoresis, no consensus method has been established for determining AAV genome purity. Disclosed herein are high-throughput methods to assess AAV vector genome purity and structure with high sensitivity and high reproducibility by Size Exclusion Chromatography (SEC).

AAV vector genome is a single-stranded DNA (ssDNA) with individual AAV particles comprising the plus- or the minus-strand DNA genomes with equal frequency. Once released from AAV vectors, the plus- and minus-strand single-stranded DNA genomes may anneal spontaneously to form double-stranded DNA (dsDNA). The formation of dsDNA is dependent on the denaturing conditions used to release the single-stranded genomes. At low temperature, where denaturation is incomplete, ssDNA with different secondary structures can be detected by SEC in addition to dsDNA. Under a complete denaturing condition at higher temperature, all ssDNA was converted to dsDNA. Surprisingly, further increasing denaturation temperature above a sample specific optimum results in a loss of signal during SEC. Without being bound by any particular theory, incubation at these above optimum temperatures, i.e., at 90° C. and 95° C. may cause loss of material and/or may create artificial DNA fragments. The observed material loss and fragmentation indicates an AAV vector genome thermos-instability, which may vary from AAV product to product, and is probably related to vector sequence and DNA construct designs.

In addition to AAV product to AAV product variation, the response to thermal denaturation may also vary between AAV subpopulations within the same product. For example, certain AAV subpopulations isolated from anion-exchange chromatography displayed an increased resistance to denaturation, suggesting these AAV vectors may contain ssDNA with a compact structure. Genome content of these AAV vectors determined by ddPCR was lower than that determined by spectrophotometry or SEC quantification, indicating the presence of compact DNA structures and the need for further denaturation for improved PCR efficiency.

Upon complete denaturation at the sample specific optimum temperature, all released vector genome forms dsDNA, which can be separated by SEC from impurities including host cell residual DNA, plasmid DNA, and genome fragments. Analysis of the released DNA from AAV by SEC provides a quantitative assessment of the size purity of the AAV vector genome. The percentage of DNA fragments determined by this method correlates well with the percentage of partially-filled capsids determined by AUC. AUC analysis is time-consuming, requiring advanced techniques and knowledge for system operation and data analysis, and often consuming a large sample size. In contrast, purity analysis by SEC as disclosed herein is fast, reproducible, highly sensitive with improved Limit of Quantitation (LoQ), and can be automated for high throughput analysis. FIG. 1 (see also FIG. 9). The SEC method disclosed herein was used for quick assessment of the partially-filled capsids to support product development and process optimization, and as an orthogonal method for AAV product characterization. In addition, vector genome titers could be determined using the peak area detected by this SEC method with UV absorbance at 260 nm.

Figures 2A, 2B:
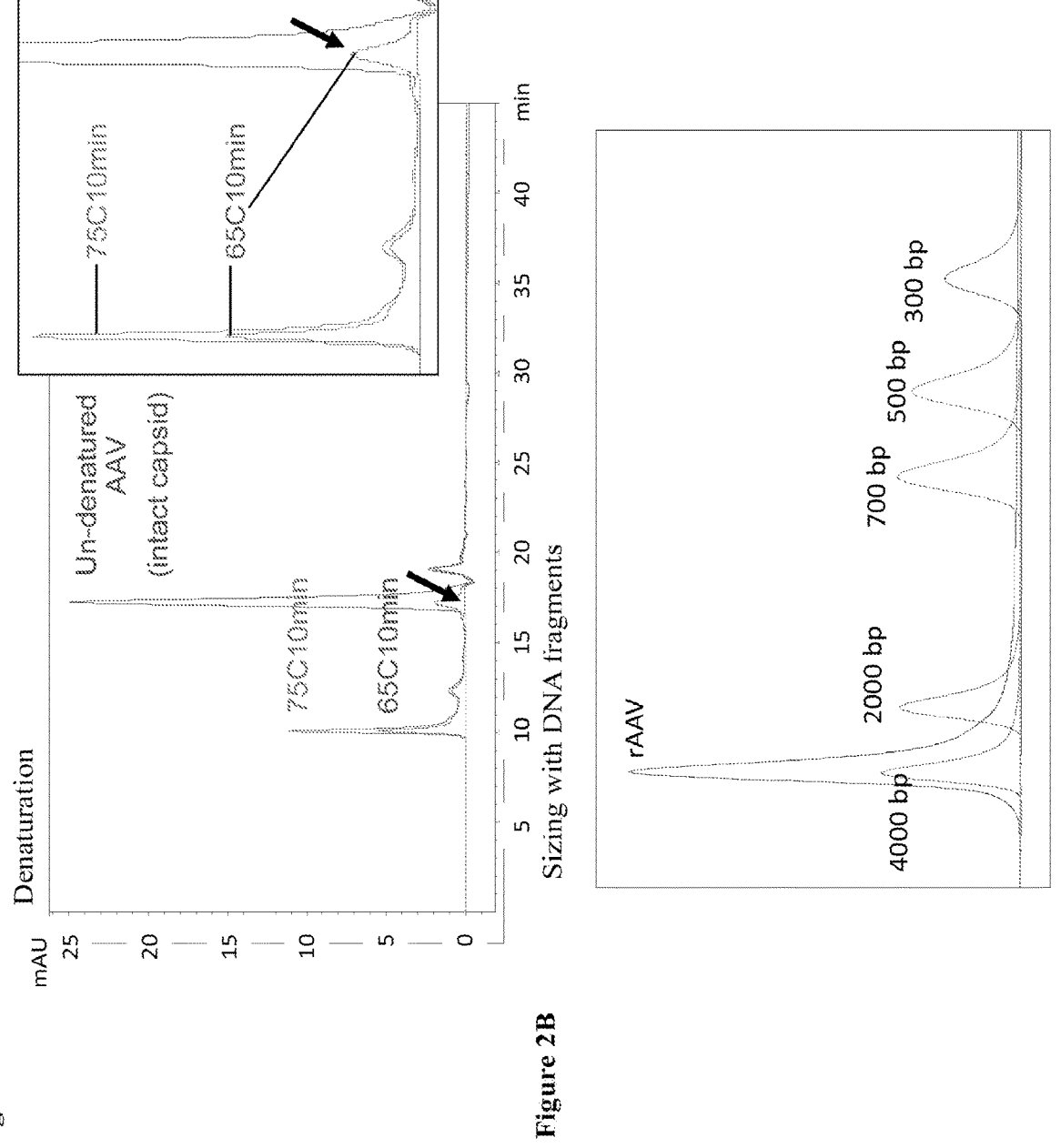
FIGS. 2A and 2B. Denaturation of rAAV capsids.
Figure 3:
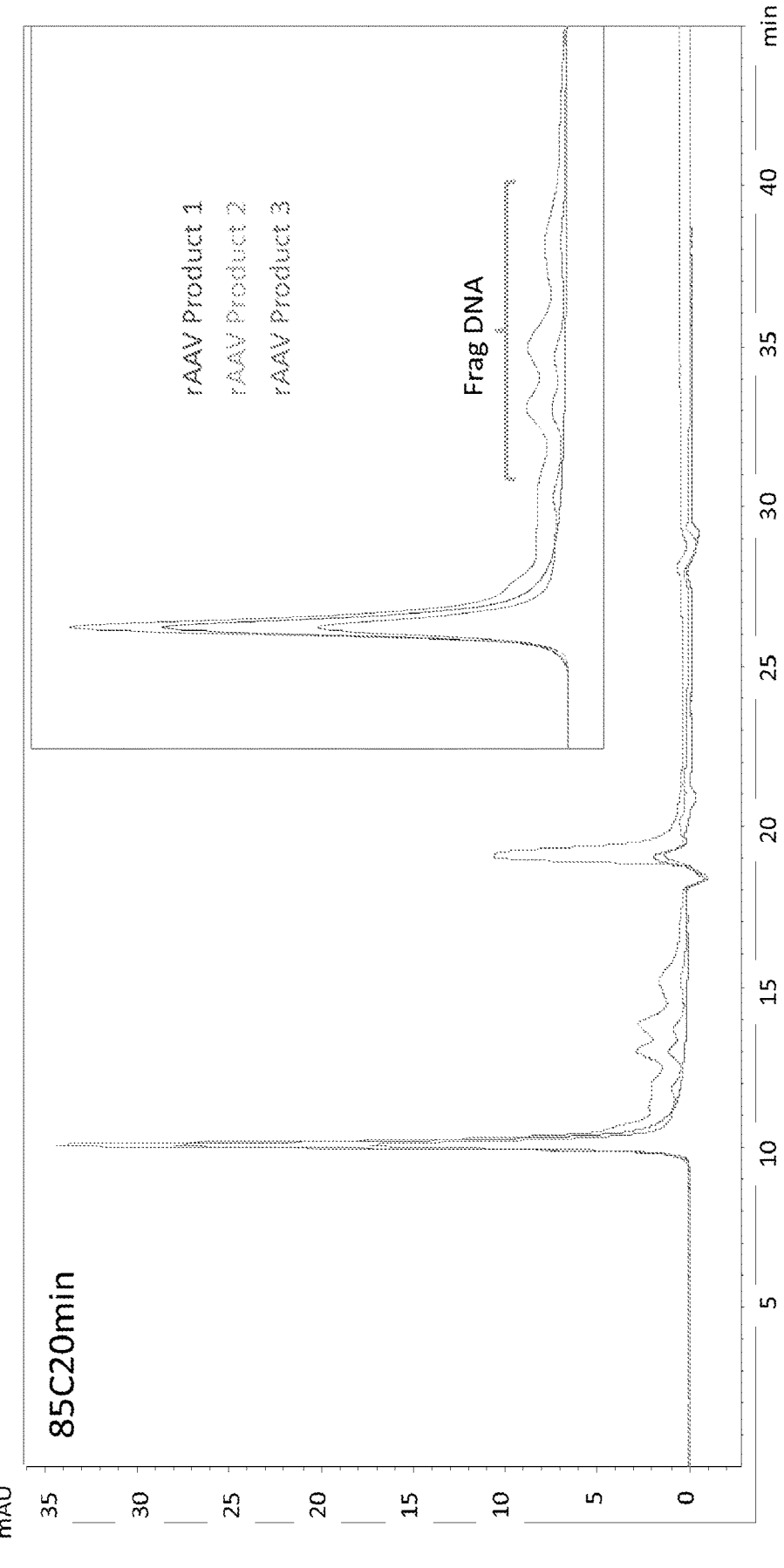
FIG. 3. Overlaid chromatograms for three different rAAV products. Samples were denatured by incubation at 80° C. for 20 minutes in the presence of 0.05% SDS.

Sample preparation. 20 to 40 μL of AAV vector samples were heated to desired temperatures in the presence of 0.05% SDS on a heat block. By using appropriate heating blocks, multiple samples, e.g., up to 50-100 samples can be prepared. Optimal temperature and duration for thermal denaturation were evaluated by time course studies and determined for each AAV vector product individually as verified by complete disruption of the intact AAV peak and appearance of the pure vector genome DNA and fragment DNA peaks on SEC. FIGS. 2 and 3.

Size-exclusion HPLC. Size-exclusion HPLC (SEC) was performed on an Agilent 1290 UHPLC system (Agilent). Injection volume was based on the estimated genome concentration of the sample. For samples >5E+12 GC/mL, 10 µLin injected and for samples below <5E+12 GC/mL, 15-20 µL is injected for analysis. UV absorbance at 280 nm and 260 nm were monitored using a diode array detector with a 6 cm path length flow cell. A fluorescence detector was used to confirm the purity of DNA. About 5×10$^{10}$ GC heat-denatured AAV vector sample was loaded onto a SRT SEC2000 (300×4.6 mm, I.D., pore size 2000 nm) SEC column (SEPAX) at ambient temperature. An isocratic gradient using a mobile phase of 10 mM sodium phosphate, 300 mM sodium chloride, 0.05% polysorbate 80, 20% methanol, pH 7.5 at a flow rate of 0.2 ml/min for a total run time of 45 minutes was used to measure each sample. Data analysis was performed using OpenLAB software (Agilent). FIG. 3 shows the SEC profiles of 3 separate products run in the same sequence.

Example 2. Denaturation and Structure Characterization of ssDNA

Figure 4:
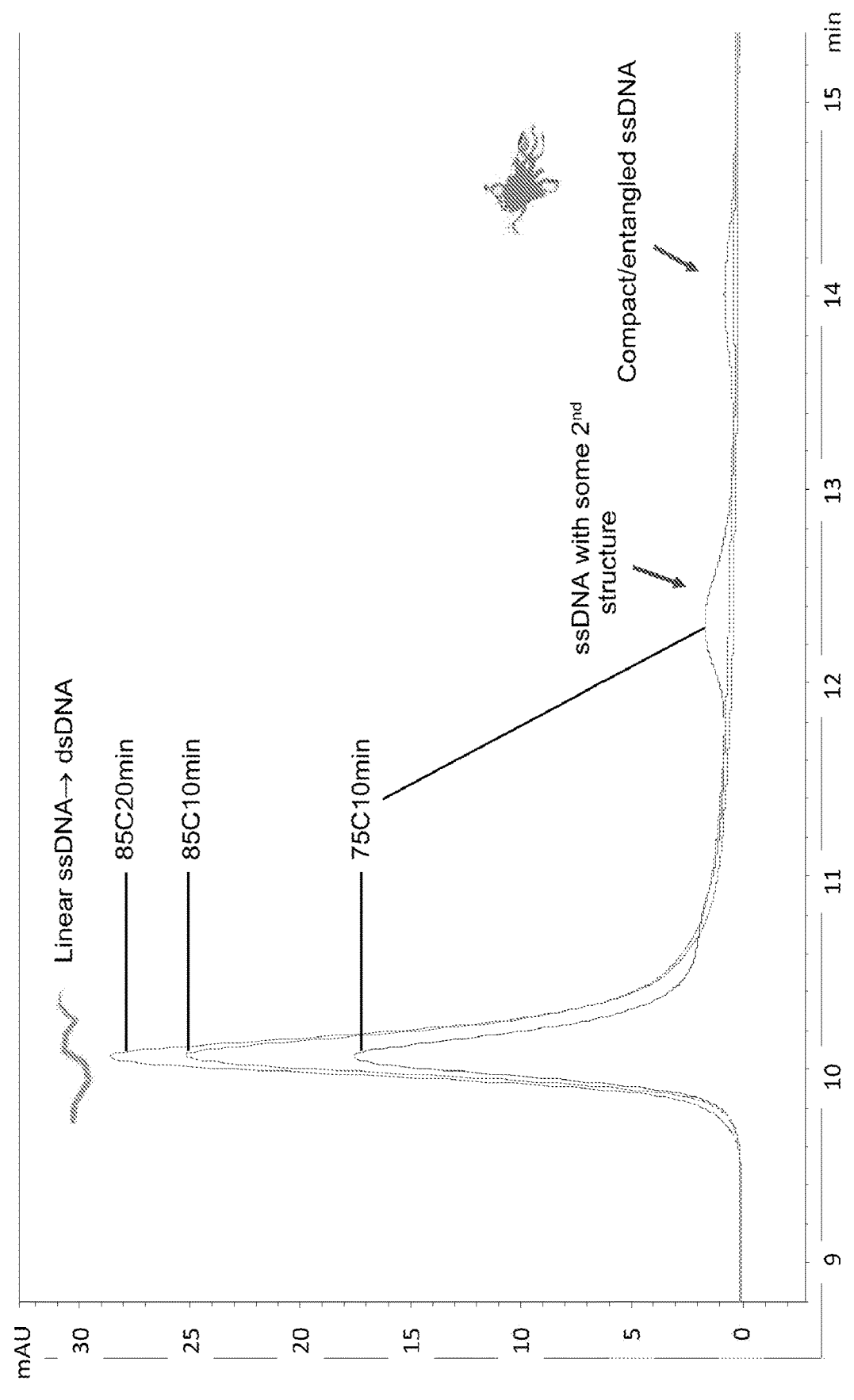
FIG. 4. Denaturation and structure characterization of ssDNA. SEC profile of an rAAV sample exposed to 75° C. for 10 min, 85° C. for 10 min, or 85° C. for 20 min in the presence of 0.05% SDS is shown. The presence of ssDNA in the sample exposed to 75° C. for 10 min indicates that it was not completely denatured by the heat treatment. 85° C. for 20 min was optimal for denaturing/linearizing ssDNA. Low amount of truncated vector genome could be observed in all samples.

SEC profile of an rAAV sample was analyzed following denaturation at 75° C. for 10 min, 85° C. for 10 min, or 85° C. for 20 min. FIG. 4. The presence of ssDNA with some secondary structure in the sample exposed to 75° C. for 10 min indicates that it was not completely denatured by the heat treatment. 85° C. for 20 min was optimal for completely denaturing/linearizing ssDNA. Low amount of truncated vector genome could be observed in all three samples. SEC analysis of different preparations of the same rAAV following denaturation at 75° C. for 10 min showed that the level of ssDNA with some secondary structure varied between the different preparations.

Example 3. Excessive Thermal Denaturation Leads to Signal Loss

Figure 5:
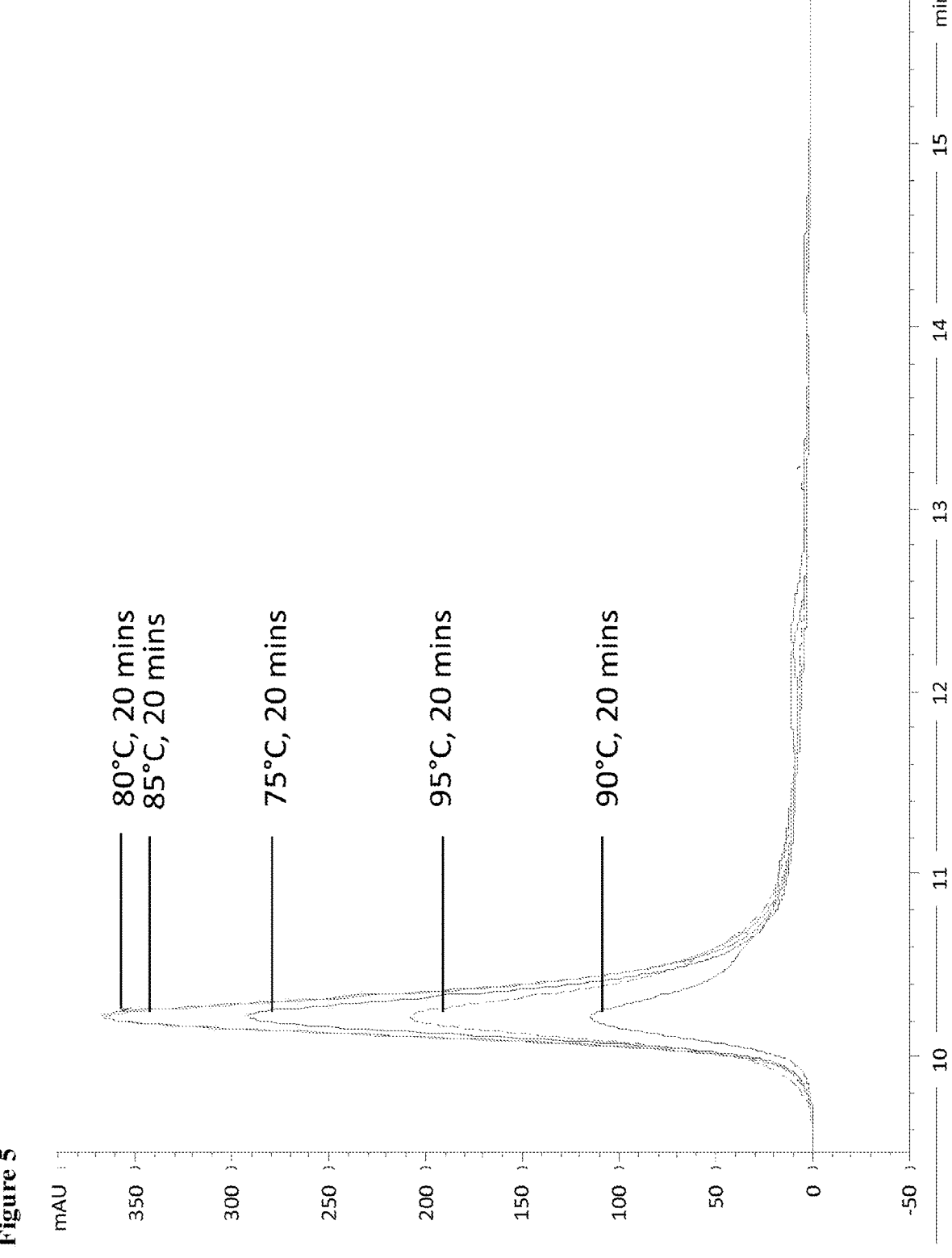
FIG. 5. UV260 absorbance curve of an AAV preparation following thermal denaturation at 75° C., 80° C., 85° C., 90° C., 95° C. for 20 min.

SEC profile of a rAAV sample was analyzed following thermal denaturation at 75° C., 80° C., 85° C., 90° C., or 95° C. for 20 min. FIG. 5. Signal intensity for dsDNA was higher following thermal denaturation at 80° C. and 85° C. than at 75° C., as expected based on, for example, the data shown in Example 2. Surprisingly, a further increase in the thermal denaturation temperature to 90° C. and 95° C. resulted in a loss of dsDNA signal. These results indicated that there was an optimal thermal denaturation temperature leading to a maximum signal, and that the optimal thermal denaturation temperature for the particular sample tested was in the range of about 80° C. to about 85° C. This observation was surprising because a 20 minute incubation at 90° C. and 95° C. was not expected to significantly degrade the AAV genome. Without being bound by any particular theory, incubation at the higher temperatures, i.e., at 90° C. and 95° C. may have caused loss of material and/or may have created artificial DNA fragments. The observed material loss and fragmentation indicated an AAV vector genome thermo-instability, which may vary from AAV product to product, and is probably related to vector sequence and DNA construct designs.

Determining the product specific optimal thermal denaturation conditions are important for developing a high-throughput screening assay using the methods disclosed herein. As demonstrated in the Examples below, the assay described herein is useful, for example, as an orthogonal method to AUC to quantitate the ratio of partially filled rAAV particles comprising truncated vector genome. Reliably good correlation between % Fragment DNA determined by DNA-SEC and % Partial-filled capsid determined by AUC can be achieved by using the product specific optimal thermal denaturation conditions for the DNA-SEC assay disclosed herein.

Figures 6, 7:
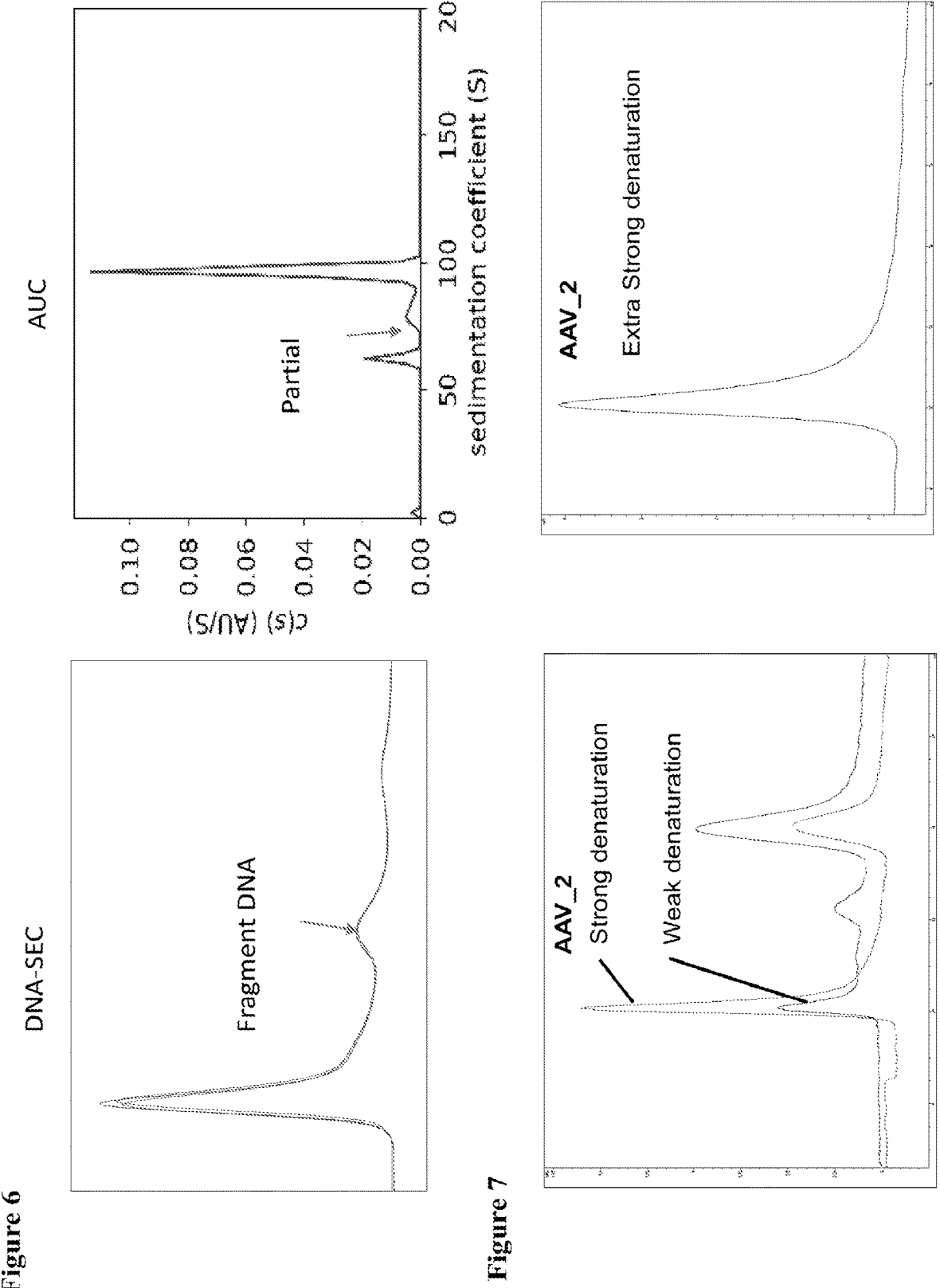
FIG. 6. Comparison of % Fragment DNA by DNA-SEC vs. % Partial by Analytical Ultracentrifugation.
FIG. 7. UV260 absorbance curve of an AAV preparation following weak, strong and extra strong denaturation.

Example 4. Bridging Analysis of Truncated Vector Genome Between AUC and DNA-SEC Low level of fragmented DNA was observed in compositions comprising three different rAAV particles following complete denaturation by treatment at 85° C. for 20 min. FIG. 3. The level of partially filled rAAV particles as determined by AUC and the level of fragmented DNA detected by DNA-SEC showed consistent results. FIG. 6. Thus, the DNA-SEC method disclosed herein can be used as a high-throughput orthogonal method to AUC to quantitate the ratio of partially filled rAAV particles comprising truncated vector genome.

| Sample | % Frag DNA by SEC | % Partial by AUC |
|---|---|---|
| AAV Product 1 | 3.9 | 3.0 |
| AAV Product 2 | 7.7 | 8.9 |
| AAV Product 3 | 5.6 | 5.2 |

The good correlation between % Fragment DNA determined by DNA-SEC and % Partial-filled capsid determined by AUC demonstrates that DNA-SEC can be used to quickly assess the level of partially-filled capsids in a large number of samples to support product development and process optimization.

Example 5. VGC Titer by ddPCR and DNA-SEC

Viral genome copy (VGC) titer was determined for multiple rAAV preparations using DNA-SEC disclosed herein and ddPCR. DNA-SEC and ddPCR showed overall consistent VGC titer results for AAV products.

An advantage of the methods disclosed herein is that for rAAV compositions with high amount of truncated genome, VGC titer by DNA-SEC is capable of reporting VGC for full-length vector genome.

Example 6. Characterization of Folding of AAV Vector Genomes

Certain AAV populations, for example, AAV populations isolated from anion-exchange chromatography (AAV_2 in FIG. 7) displayed an increased resistance to denaturation. Genome content of these AAV vectors determined by ddPCR was lower than those determined by spectrophotometry or SEC quantification, indicating the presence of compact DNA structures and the need for further denaturation for improved PCR efficiency. As demonstrated herein, by using various denaturing conditions, the DNA-SEC method disclosed herein can be used to provide information on the secondary structure/folding of AAV vector genome inside capsids, which can potentially impact efficiency of PCR-based assays and potency.

Example 7. Process Optimization Assessed by DNA-SEC

Figure 8:
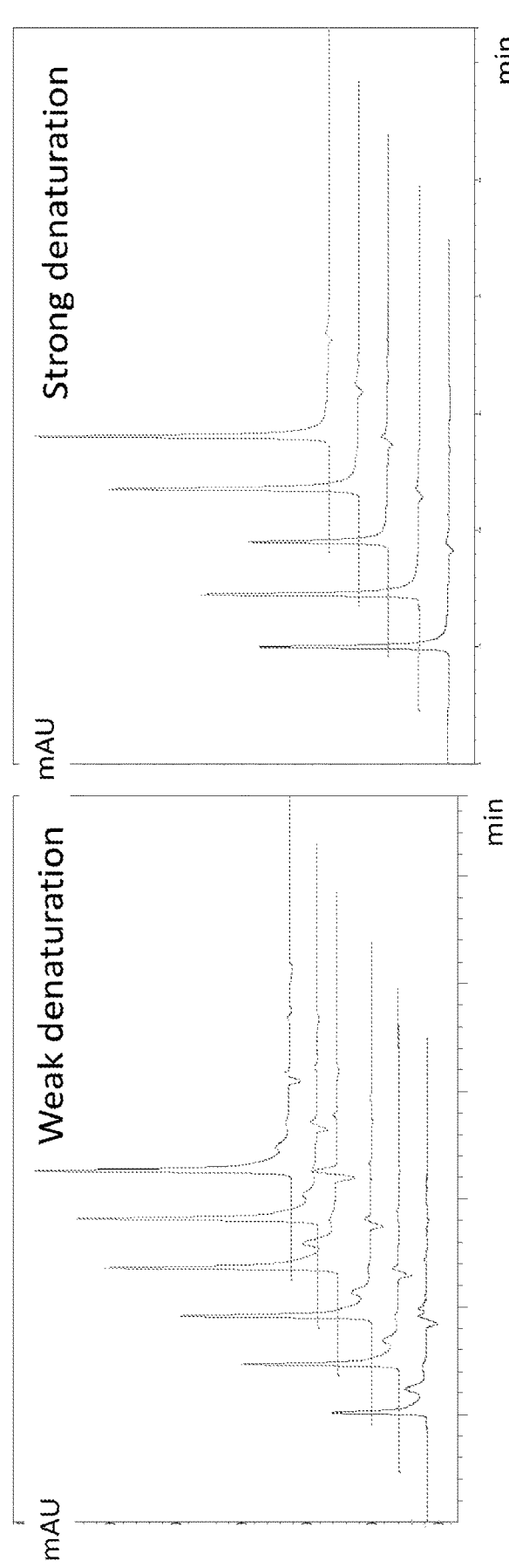
FIG. 8. Process Optimization Assessed by DNA-SEC.

DNA-SEC can be used as a high-throughput screening assay to support process optimization and product characterization. FIG. 8 shows the DNA-SEC profile of 5 rAAV preparations produced by 5 different optimized processes.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

```
                          SEQUENCE LISTING

<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Recombinant polypeptide

<400> SEQUENCE: 1

Leu Gly Glu Thr Thr Arg Pro
1               5

<210> SEQ ID NO 2
<211> LENGTH: 9
<212> TYPE: PRT
<213> ORGANISM: Artificial Sequence
<220> FEATURE:
<223> OTHER INFORMATION: Recombinant polypeptide

<400> SEQUENCE: 2

Leu Ala Leu Gly Glu Thr Thr Arg Pro
1               5
```

DNA-SEC profiles were determined following both weak and strong denaturation. The % of genome fragments varied between 3.9% and 7.7% among the 5 rAAV preparations.

| Process | % Fragment DNA by SEC |
|---|---|
| Process_1 | 3.9 |
| Process_2 | 4.1 |
| Process_3 | 7.7 |
| Process_4 | 5.6 |
| Process_5 | 5.6 |

Example 8. Performance Assessment of DNA-SEC Assay

Figures 9A, 9B, 9C:
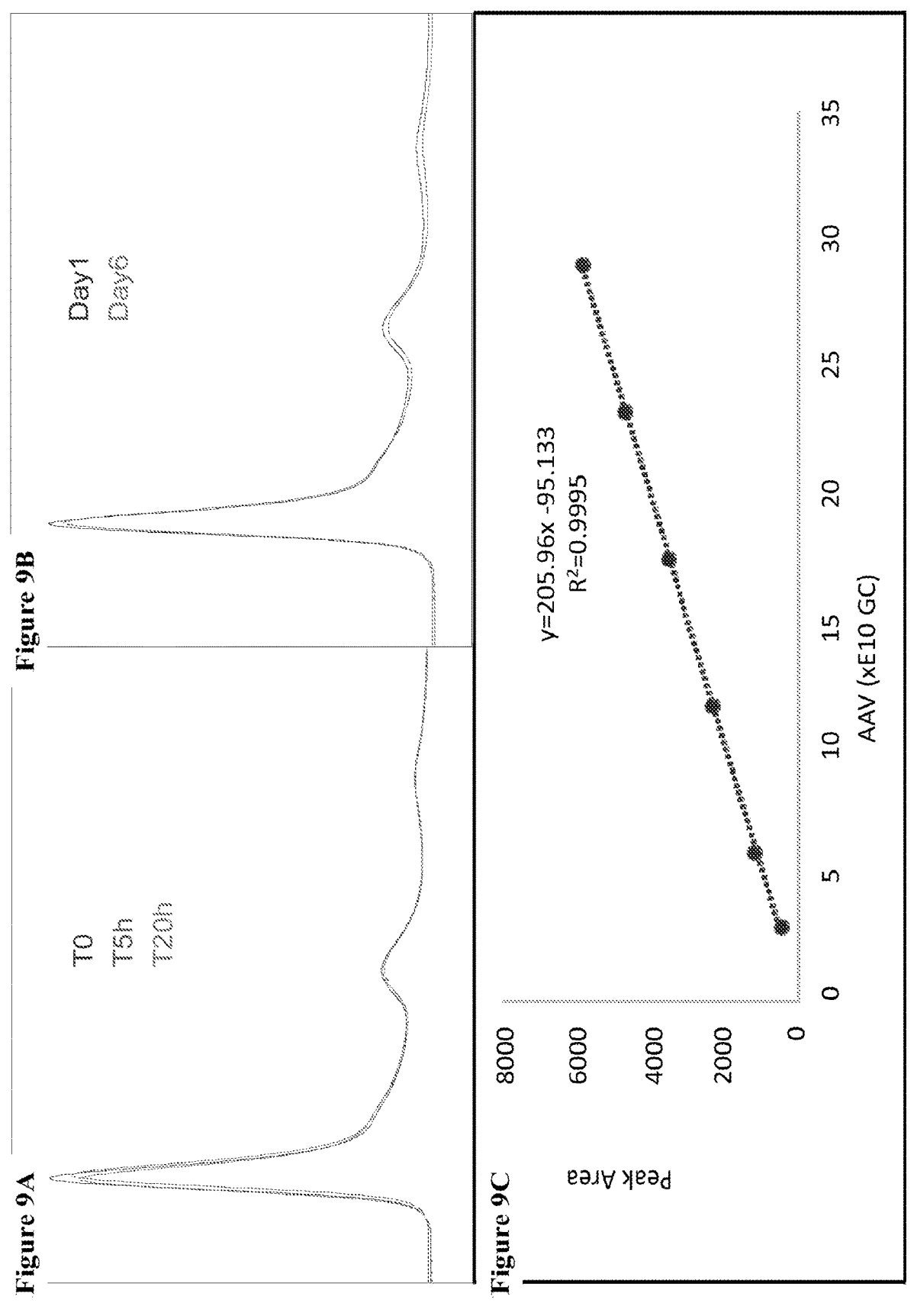
FIGS. 9A-C. Assay performance measures were performed with respect to precision (FIG. 9A and FIG. 9B), linearity and LoQ (FIG. 9C). The tested parameters demonstrate an overall reliability and sensitivity of the DNA-SEC assay.

The DNA-SEC assay described herein provides a reliable method and was tested for performance with respect to precision, linearity and Limit of Quantitation (LoQ). Reproducibility were within 5% repeatability during the same SEC run, within 10% intermediate precision. The assay demonstrated linearity, with detection in the range of 2.9E+10 to 29E+10 GC of AAV, and LoQ~ 2E+10 GC of AAV. FIG. 9.

While the disclosed methods have been described in connection with what is presently considered to be the most practical and preferred embodiments, it is to be understood that the methods encompassed by the disclosure are not to be limited to the disclosed embodiments, but on the contrary, is intended to cover various modifications and equivalent arrangements included within the spirit and scope of the appended claims.

What is claimed is:

1. A method of isolating recombinant adeno associated virus (rAAV) genome comprising
   a) subjecting a composition comprising rAAV particles to a condition under which the rAAV particles are denatured;
   b) subjecting the composition comprising the denatured rAAV particles to size exclusion chromatography (SEC), wherein the SEC produces an eluate; and
   c) detecting DNA in the eluate by spectrophotometry, wherein the mobile phase for the SEC comprises a salt, organic solvent, or detergent.

2. The method of claim 1, further comprising recovering the AAV genome.

3. The method of claim 1, wherein the detecting DNA in the eluate by spectrophotometry comprises measuring the eluate's UV absorbance at one or both of about 260 nm and at about 280 nm.

4. A method of determining the vector genome size uniformity of a composition comprising isolated rAAV particles, wherein the method comprises
   a) subjecting the composition to a condition under which the rAAV particles are denatured;
   b) subjecting the composition comprising the denatured rAAV particles to size exclusion chromatography (SEC), wherein the SEC produces an eluate;
   c) measuring the eluate's UV absorbance at one or both of about 260 nm and at about 280 nm; and
   d) determining the vector genome size uniformity of the composition comprising rAAV particles, wherein the mobile phase for the SEC comprises a salt, organic solvent, or detergent.

5. A method of assessing the folding or secondary structure of AAV vector genomes inside the capsids, wherein the method comprises a) subjecting the composition to a condition under which the rAAV particles are denatured;

b) subjecting the composition comprising the denatured rAAV particles to size exclusion chromatography (SEC), wherein the SEC produces an eluate; and c) measuring the eluate's UV absorbance at one or both of about 260 nm and at about 280 nm, wherein the mobile phase for the SEC comprises a salt, organic solvent, or detergent.

6. A method of determining vector genome titer (Vg) of a composition comprising isolated rAAV particles, wherein the method comprises a) subjecting the composition to a condition under which the rAAV particles are denatured;

b) subjecting the composition comprising the denatured rAAV particles to size exclusion chromatography (SEC), wherein the SEC produces an eluate;

c) measuring the eluate's UV absorbance at one or both of about 260 nm and at about 280 nm; and d) determining the Vg of the composition comprising rAAV particles, wherein the mobile phase for the SEC comprises a salt, organic solvent, or detergent.

7. The method of claim 1, wherein subjecting the composition to a condition under which the rAAV particles are denatured comprises a) exposing the composition to a condition that substantially maximizes the dsDNA signal detectable during SEC;

b) exposing the composition to a temperature that is no more than 10° C. above the minimum temperature needed to denature substantially all viral particles in the composition;

c) subjecting the composition to a condition that results in a % Fragment DNA determination that correlates with the % Partial-filled capsid of the same composition determined by analytical ultracentrifugation (AUC);

d) exposing the composition to thermal denaturation that substantially maximizes the dsDNA signal detectable during SEC; or e) subjecting the composition to thermal denaturation that results in a % Fragment DNA determination that correlates with the % Partial-filled capsid of the same composition determined by AUC.

8. The method of claim 1, wherein subjecting the composition to a condition under which the rAAV particles are denatured comprises a) incubating the composition at a temperature between about 65° C. and about 95° C.;

b) incubating the composition at a temperature between about 65° C. and about 95° C. for between about 5 minutes and 60 minutes; or c) incubating the composition at a temperature between about 65° C. and about 95° C. for between about 5 minutes and 60 minutes in the presence of a detergent.

9. The method of claim 4, wherein the mobile phase for the SEC comprises a salt, organic solvent, and detergent.

10. The method of claim 4, wherein the mobile phase comprises between about 5 mM and about 50 mM sodium phosphate, between about 100 mM and about 500 mM sodium chloride, between about 0.01% and about 0.5% polysorbate 80, and between about 5% and about 50% methanol, and has a pH between about 6.0 and 8.5.

11. The method of claim 4, wherein subjecting the composition to a condition under which the rAAV particles are denatured comprises a) exposing the composition to a condition that substantially maximizes the dsDNA signal detectable during SEC;

b) exposing the composition to a temperature that is no more than 10° C. above the minimum temperature needed to denature substantially all viral particles in the composition;

c) subjecting the composition to a condition that results in a % Fragment DNA determination that correlates with the % Partial-filled capsid of the same composition determined by analytical ultracentrifugation (AUC);

d) exposing the composition to thermal denaturation that substantially maximizes the dsDNA signal detectable during SEC; or e) subjecting the composition to thermal denaturation that results in a % Fragment DNA determination that correlates with the % Partial-filled capsid of the same composition determined by AUC.

12. The method of claim 4, wherein subjecting the composition to a condition under which the rAAV particles are denatured comprises incubating the composition at a temperature between about 65° C. and about 95° C.

13. The method of claim 12, wherein at least about 95% of the viral particles in the sample are denatured by the denaturation process.

14. The method of claim 12, wherein subjecting the composition to a condition under which the rAAV particles are denatured comprises incubating the composition at a temperature between about 65° C. and about 95° C. for between about 5 minutes and 60 minutes.

15. The method of claim 12, wherein subjecting the composition to a condition under which the rAAV particles are denatured comprises incubating the composition at a temperature between about 65° C. and about 95° C. for between about 5 minutes and 60 minutes in the presence of a detergent.

16. The method of claim 15, wherein the detergent comprises sodium dodecyl sulfate (SDS), trimethyl ammonium bromide (ETMAB), polysorbate 80, polysorbate 20, poloxamer 188, or a combination thereof.

17. The method of claim 4, wherein the mobile phase comprises between about 5 mM and about 50 mM sodium phosphate, between about 100 mM and about 500 mM sodium chloride, between about 0.01% and about 0.5% polysorbate 80, and between about 5% and about 50% methanol, and has a pH between about 6.0 and 8.5.

18. The method of claim 5, wherein subjecting the composition to a condition under which the rAAV particles are denatured comprises a) incubating the composition at a temperature between about 65° C. and about 95° C.;

b) incubating the composition at a temperature between about 65° C. and about 95° C. for between about 5 minutes and 60 minutes; or c) incubating the composition at a temperature between about 65° C. and about 95° C. for between about 5 minutes and 60 minutes in the presence of a detergent.

19. The method of claim 6, wherein subjecting the composition to a condition under which the rAAV particles are denatured comprises a) incubating the composition at a temperature between about 65° C. and about 95° C.;

b) incubating the composition at a temperature between about 65° C. and about 95° C. for between about 5 minutes and 60 minutes; or c) incubating the composition at a temperature between about 65° C. and about 95° C. for between about 5 minutes and 60 minutes in the presence of a detergent.

20. The method of claim 6, wherein the mobile phase comprises between about 5 mM and about 50 mM sodium phosphate, between about 100 mM and about 500 mM sodium chloride, between about 0.01% and about 0.5% polysorbate 80, and between about 5% and about 50% methanol, and has a pH between about 6.0 and 8.5.

\* \* \* \* \*